(12) United States Patent
Braganca et al.

(10) Patent No.: US 11,932,904 B2
(45) Date of Patent: *Mar. 19, 2024

(54) ENHANCED OPTICAL DETECTION FOR NUCLEIC ACID SEQUENCING USING THERMALLY-DEPENDENT FLUOROPHORE TAGS

(71) Applicant: Western Digital Technologies, Inc., San Jose, CA (US)

(72) Inventors: Patrick Braganca, San Jose, CA (US); Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 309 days.

This patent is subject to a terminal disclaimer.

(21) Appl. No.: 17/457,404

(22) Filed: Dec. 2, 2021

(65) Prior Publication Data

US 2022/0090173 A1 Mar. 24, 2022

Related U.S. Application Data

(63) Continuation of application No. 16/569,823, filed on Sep. 13, 2019, now Pat. No. 11,208,682.

(51) Int. Cl.
*C12Q 1/6816* (2018.01)
*B01L 3/00* (2006.01)
*B01L 7/00* (2006.01)

(52) U.S. Cl.
CPC .......... *C12Q 1/6816* (2013.01); *B01L 3/502* (2013.01); *B01L 7/52* (2013.01); *B01L 2200/147* (2013.01); *B01L 2300/0663* (2013.01); *B01L 2300/1805* (2013.01)

(58) Field of Classification Search
CPC .............. C12Q 1/6816; C12Q 1/6869; C12Q 2527/101; C12Q 2563/107; B01L 3/502; B01L 7/52; B01L 2200/147; B01L 2300/0663; B01L 2300/1805
See application file for complete search history.

(56) References Cited

U.S. PATENT DOCUMENTS

| | | |
|---|---|---|
| 5,200,084 A | 4/1993 | Liberti et al. |
| 5,302,509 A | 4/1994 | Cheeseman |
| 6,037,167 A | 3/2000 | Adelman et al. |
| 6,046,585 A | 4/2000 | Simmonds |
| 6,197,520 B1 | 3/2001 | Wittwer et al. |
| 6,406,848 B1 | 6/2002 | Bridgham et al. |
| 6,654,505 B2 | 11/2003 | Bridgham et al. |
| 6,806,052 B2 | 10/2004 | Bridgham et al. |
| 6,831,994 B2 | 12/2004 | Bridgham et al. |
| 6,833,246 B2 | 12/2004 | Balasubramanian |
| 6,905,736 B1 | 6/2005 | Chow et al. |
| 6,969,488 B2 | 11/2005 | Bridgham et al. |
| 6,969,679 B2 | 11/2005 | Okamura et al. |
| 7,057,026 B2 | 6/2006 | Barnes et al. |
| 7,115,400 B1 | 10/2006 | Adessi et al. |
| 7,282,370 B2 | 10/2007 | Bridgham et al. |
| 7,382,586 B2 | 6/2008 | Carey et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,473,031 B2 | 1/2009 | Wolkin et al. |
| 7,541,444 B2 | 6/2009 | Milton et al. |
| 7,566,537 B2 | 7/2009 | Balasubramanian et al. |
| 7,771,973 B2 | 8/2010 | Milton et al. |
| 7,772,384 B2 | 8/2010 | Balasubramanian et al. |
| 7,920,032 B2 | 4/2011 | Makinwa et al. |
| 8,053,244 B2 | 11/2011 | Ryan et al. |
| 8,058,031 B2 | 11/2011 | Xu et al. |
| 8,071,739 B2 | 12/2011 | Milton et al. |
| 8,130,072 B2 | 3/2012 | De Bruyker et al. |
| 8,158,346 B2 | 4/2012 | Balasubramanian et al. |
| 8,252,910 B2 | 8/2012 | Korlach et al. |
| 8,259,409 B2 | 9/2012 | Braganca et al. |
| 8,361,713 B2 | 1/2013 | Bridgham et al. |
| 8,367,813 B2 | 2/2013 | Korlach |
| 8,432,644 B2 | 4/2013 | Braganca et al. |
| 8,462,461 B2 | 6/2013 | Braganca et al. |

(Continued)

FOREIGN PATENT DOCUMENTS

| | | |
|---|---|---|
| CN | 102928596 A | 2/2013 |
| CN | 103885000 A | 6/2014 |

(Continued)

OTHER PUBLICATIONS

A. Seki, et al., "Study of the heating characteristics and mechanisms of magnetic nanoparticles over a wide range of frequencies and amplitudes of an alternating magnetic field," Journal of Physics: Conference Series 521 (2014).

A.M. Sydor et al., "Super-Resolution Microscopy: From Single Molecules to Supramolecular Assemblies," Trends in Cell Biology, Dec. 2015, vol. 25, No. 12, pp. 730-748.

B. N. Engel, et al., "A 4-Mb Toggle MRAM Based on a Novel Bit and Switching Method," IEEE Transactions On Magnetics, vol. 41, No. 1, Jan. 2005.

C. Chappert et al., "The emergence of spin electronics in data storage," Nature Materials, Dec. 2007.

(Continued)

*Primary Examiner* — Narayan K Bhat

(57) ABSTRACT

Disclosed herein are improved methods and systems for sequencing nucleic acid that exploit the temperature-dependence of the emitted intensity of fluorescent dyes. The temperature of the sequencing reaction is adjusted during each sequencing cycle, and the emission, or lack of emission, of light meeting or exceeding a threshold by the fluorescent dyes at different temperatures, or within different temperature ranges, is used to detect the fluorescent labels of the incorporated dNTPs and thereby sequence the nucleic acid. The disclosed methods enable a determination of the dNTP incorporated at any given site with a reasonable number of chemistry steps without the complex optics necessary for prior-art systems.

20 Claims, 12 Drawing Sheets

(56) References Cited

U.S. PATENT DOCUMENTS

| | | |
|---|---|---|
| 8,513,029 B2 | 8/2013 | Zhou |
| 8,553,346 B2 | 10/2013 | Braganca et al. |
| 8,570,677 B2 | 10/2013 | Braganca et al. |
| 8,597,881 B2 | 12/2013 | Milton et al. |
| 8,652,810 B2 | 2/2014 | Adessi et al. |
| 8,654,465 B2 | 2/2014 | Braganca et al. |
| 8,675,309 B2 | 3/2014 | Braganca et al. |
| 8,728,729 B2 | 5/2014 | Bridgham et al. |
| 8,728,825 B2 | 5/2014 | Wang et al. |
| 9,121,062 B2 | 9/2015 | Balasubramanian et al. |
| 9,273,354 B2 | 3/2016 | Bridgham et al. |
| 9,297,006 B2 | 3/2016 | Adessi et al. |
| 9,435,791 B2 | 9/2016 | Acosta et al. |
| 9,453,258 B2 | 9/2016 | Kain et al. |
| 9,464,107 B2 | 10/2016 | Wegener et al. |
| 9,587,275 B2 | 3/2017 | Emig et al. |
| 9,605,310 B2 | 3/2017 | Balasubramanian et al. |
| 9,640,748 B2 | 5/2017 | Gotsmann et al. |
| 10,203,379 B2 | 2/2019 | Wang et al. |
| 10,260,095 B2 | 4/2019 | Esfandyarpour et al. |
| 10,591,440 B2 | 3/2020 | Astier et al. |
| 2004/0043479 A1 | 3/2004 | Briscoe et al. |
| 2004/0219695 A1 | 11/2004 | Fox |
| 2005/0054081 A1 | 3/2005 | Hassard et al. |
| 2005/0100930 A1 | 5/2005 | Wang et al. |
| 2005/0118102 A1 | 6/2005 | Xiang et al. |
| 2007/0224700 A1 | 9/2007 | Masters |
| 2007/0264159 A1 | 11/2007 | Graham et al. |
| 2008/0218165 A1 | 9/2008 | Kahlman et al. |
| 2008/0241569 A1 | 10/2008 | Qin et al. |
| 2009/0148857 A1 | 6/2009 | Srivastava et al. |
| 2009/0206832 A1 | 8/2009 | Kahlman et al. |
| 2009/0208957 A1 | 8/2009 | Korlach et al. |
| 2010/0039105 A1 | 2/2010 | Ryan et al. |
| 2010/0111768 A1 | 5/2010 | Banerjee et al. |
| 2010/0194386 A1 | 8/2010 | Prins et al. |
| 2010/0207631 A1 | 8/2010 | McDowell |
| 2010/0231214 A1 | 9/2010 | Zhou |
| 2010/0248973 A1 | 9/2010 | Lankvelt et al. |
| 2010/0291558 A1 | 11/2010 | Kim |
| 2011/0223612 A1 | 9/2011 | Wang et al. |
| 2012/0214171 A1 | 8/2012 | Kotseroglou |
| 2012/0295262 A1 | 11/2012 | Ronaghi et al. |
| 2014/0008281 A1 | 1/2014 | Ramanathan et al. |
| 2014/0099663 A1 | 4/2014 | Wang et al. |
| 2014/0139214 A1 | 5/2014 | Park et al. |
| 2014/0292318 A1 | 10/2014 | Wang et al. |
| 2016/0131613 A1 | 5/2016 | Jayant et al. |
| 2017/0097337 A1 | 4/2017 | Shultz et al. |
| 2017/0304825 A1 | 10/2017 | Issadore et al. |
| 2018/0074016 A1 | 3/2018 | Chen et al. |
| 2018/0100190 A1 | 4/2018 | Esfandyarpour et al. |
| 2018/0128822 A1 | 5/2018 | Wang et al. |
| 2018/0237850 A1 | 8/2018 | Mandell et al. |
| 2018/0284200 A1 | 10/2018 | Chen et al. |
| 2019/0032114 A1 | 1/2019 | Trivedi |
| 2019/0170680 A1 | 6/2019 | Sikora et al. |
| 2019/0390267 A1 | 12/2019 | Astier et al. |
| 2021/0047681 A1 | 2/2021 | Mendonsa et al. |
| 2021/0047682 A1 | 2/2021 | Mendonsa et al. |

FOREIGN PATENT DOCUMENTS

| | | |
|---|---|---|
| CN | 105112516 A | 12/2015 |
| CN | 107873060 A | 4/2018 |
| CN | 107923910 A | 4/2018 |
| CN | 108138229 A | 6/2018 |
| CN | 107051597 B | 8/2019 |
| EP | 1544310 A2 | 6/2005 |
| EP | 2674264 A2 | 12/2013 |
| EP | 3208627 A1 | 8/2017 |
| ES | 2674264 | 6/2018 |
| WO | 2005047864 A3 | 9/2005 |
| WO | 2005124345 A2 | 12/2005 |
| WO | 2007123744 A2 | 11/2007 |
| WO | 2015031691 A1 | 3/2015 |
| WO | 2016183218 A1 | 11/2016 |
| WO | 2017030999 A1 | 2/2017 |
| WO | 2017061129 A1 | 4/2017 |
| WO | 2018017884 A1 | 1/2018 |
| WO | 2018186539 A1 | 10/2018 |
| WO | 2018226876 A1 | 12/2018 |
| WO | 2019060628 A1 | 3/2019 |
| WO | 2019068204 A1 | 4/2019 |
| WO | 2020210370 A1 | 10/2020 |

OTHER PUBLICATIONS

C.H. Smith et al., "High-resolution giant magnetoresistance on-chip arrays for magnetic imaging," Journal of Applied Physics 93, 6864 (2003).

D. Ross et al., "Temperature Measurement in Microfluidic Systems Using a Temperature-Dependent Fluorescent Dye," Anal. Chem. 2001, 73, 17, 4117-4123, Jul. 24, 2001.

Daschiel et al. The holy grail of microfluidics: sub-laminar drag by layout of periodically embedded microgrooves (2013) MicrofluidNanofluid 15, 675-687.

E. du Trémolet de Lacheisserie, D. Gignoux, and M. Schlenker (editors), Magnetism: Materials and Applications, vol. 2. Springer, 2005.

E. Hall, "On a New Action of the Magnet on Electric Currents," American Journal of Mathematics, vol. 2, 287, 1879.

ePHOTOzine.com, "Complete Guide To Image Sensor Pixel Size," Aug. 2, 2016, available at https://www.ephotozine.com/article/complete-guide-to-image-sensor-pixel-size-29652.

F. Grasset et al., "Synthesis, magnetic properties, surface modification and cytotoxicity evaluation of Y3Fe5—xAlxO12 (0?x?2) garnet submicron particles for biomedical applications," Journal of Magnetism and Magnetic Materials, vol. 234, Issue 3, Sep. 2001, pp. 409-418.

F. Menges et al., "Temperature mapping of operating nanoscale devices by scanning probe thermometry," Nature Communications, 7:10874, Mar. 3, 2016.

G. Li, S. Sun, R. J. Wilson, R. L. White, N. Pourmand, S. X. Wang, "Spin valve sensors for ultrasensitive detection of superparamagnetic nanoparticles for biological applications," Sensors and Actuators, vol. 126, 98, 2006.

Illumina, "Illumina CMOS Chip and One-Channel SBS Chemistry," document No. 770-2013-054-B, 2018 (available at https://www.illumina.com/content/dam/illumina-marketing/documents/products/techspotlights/cmos-tech-note-770-2013-054.pdf).

Illumina, "NovaSeq 6000 Sequencing System," 2019, available at https://www.illumina.com/systems/sequencing-platforms/novaseq.html.

International Search Report and Written Opinion from PCT Application No. PCT/US2019/068131 (filed Dec. 20, 2019), dated Apr. 1, 2020.

International Search Report and Written Opinion from PCT Application No. PCT/US2019/068535 (filed Dec. 26, 2019), dated Apr. 26, 2020.

International Search Report and Written Opinion from PCT Application No. PCT/US2020/014707 (filed Jan. 23, 2020), dated May 11, 2020.

International Search Report and Written Opinion from PCT Application No. PCT/US2020/021776 (filed Mar. 9, 2020), dated Sep. 1, 2020.

International Search Report and Written Opinion from PCT Application No. PCT/US2020/023069 (filed Mar. 17, 2020), dated Jul. 20, 2020.

International Search Report and Written Opinion from PCT Application No. PCT/US2020/023078 (filed Mar. 17, 2020), dated Jul. 19, 2020.

International Search Report and Written Opinion from PCT Application No. PCT/US2020/027290 (filed Apr. 8, 2020), dated Jun. 25, 2020.

International Search Report and Written Opinion from PCT Application No. PCT/US2020/035915 (filed Jun. 3, 2020), dated Aug. 26, 2020.

(56) References Cited

OTHER PUBLICATIONS

International Search Report and Written Opinion from PCT Application No. PCT/US2021/021274 (filed Mar. 7, 2021), dated Sep. 28, 2021.
International Search Report and Written Opinion from PCT Application No. PCT/US2021/028263 (filed Apr. 21, 2021), dated Aug. 26, 2021.
International Search Report and Written Opinion from PCT Application No. PCT/US2021/040767 (filed Jul. 8, 2021), dated Oct. 25, 2021.
International Search Report from PCT App. No. PCT/US2016/046888, dated Oct. 26, 2016.
J. C. Slonczewski, "Current-driven excitation of magnetic multilayers," Journal of Magnetism and Magnetic Materials, vol. 159, L1, 1996.
J. Sakakibara et al., "Measurements of thermally stratified pipe flow using image-processing techniques," Experiments in Fluids, Dec. 1993, vol. 16, Issue 2, pp. 82-96.
John Pearce, et al., "Magnetic Heating of Nanoparticles: The Importance of Particle Clustering to Achieve Therapeutic Temperatures," Journal of Nanotechnology in Engineering and Medicine, Feb. 2014, vol. 4 / 011007-1.
L. Berger, "Emission of spin waves by a magnetic multilayer traversed by a current," Physical Review B, vol. 54, 9353, 1996.
Lany, M., G. Boero, and R. S. Popovic. "Superparamagnetic microbead inductive detector". Review of scientific instruments 76.8 (2005): 084301.
Latha, G., Kumar, P. D., Gopi, K., Srikanth, P., Kusumalatha, Y., & Babu, G. V. (2017). A review on magnetic micro/nanoparticles. World J. Pharm. Res, 6, 341-366.
Lin Gui and Carolyn L. Ren, "Temperature measurement in microfluidic chips using photobleaching of a fluorescent thin film," Applied Physics Letters 92, 024102, 2008.
M. Aslam et al., "Silica encapsulation and magnetic properties of FePt nanoparticles," Journal of Colloid and Interface Science 290 (2005) 444-449.
M. Díaz-Michelena, "Small Magnetic Sensors for Space Applications," Sensors, vol. 9, 2271, 2009.
M. Hisham Alnasir et al., "Magnetic and magnetothermal studies of pure and doped gadolinium silicide nanoparticles for self-controlled hyperthermia applications," Journal of Magnetism and Magnetic Materials, vol. 449, Mar. 1, 2018, pp. 137-144.
M.T. Tlili et al., "Magnetic, Electrical Properties and Spin-Glass Effect of Substitution of Ca for Pr in Ca2—xPrxMnO4 Compounds," The Open Surface Science Journal, 2009, vol. 1, pp. 54-58.
Mao et al. A Microfluidic Device with a Linear Temperature Gradient for Parallel and Combinatorial Measurements (2002) J AmChem Soc 124, 4432-4435.
Michael L. Metzker, "Sequencing Technologies—the Next Generation," Nature Rev. Genet. 11: 31-46 (2009).
Miller, M. M., et al. "A DNA array sensor utilizing magnetic microbeads and magnetoelectronic detection". Journal of Magnetism and Magnetic Materials 225.1-2 (2001): 138-144.
N. X. Phuc, et al., "Tuning of the Curie Temperature in La1—xSrxMn1—yTiyO3" J. Korean Phy. Soc., vol. 52, No. 5, May 2008, pp. 1492-1495.
N.R. Patil et al., "Effect of temperature on the fluorescence emission of ENCTTTC in different nonpolar solvents," Can. J. Phys. 91: 971-975 (2013).
P. Anderson, J. Rowell, "Probable Observation of the Josephson Superconducting Tunneling Effect," Physical Review Letters, vol. 10, 230, 1963.
P. M. Braganca, B. A. Gurney, B. A. Wilson, J. A. Katine, S. Maat and J. R. Childress, "Nanoscale magnetic field detection using a spin torque oscillator," Nanotechnology, vol. 21, 235202, 2010.
P. Namdari, H. Daraee, and A. Eatemadi, "Recent Advances in Silicon Nanowire Biosensors: Synthesis Methods, Properties and Applications", Nanoscale Research Letters, vol. 11, 406, 2016.
Qiu et al. Instrument-free point-of-care molecular diagnosis of H 1 N 1 based on microfluidic convective PCR (2017) Sensors andActuators B: Chemical 243, 738-744.
Quynh, L. K., et al. Detection of magnetic nanoparticles using simple AMR sensors in Wheatstone bridge. Journal of Science: Advanced Materials and Devices, 2016, 1.1: 98-102.
R. C. Jaklevic, J. Lambe, A. H. Silver & J. E. Mercereau, "Quantum Interference Effects in Josephson Tunneling," Physical Review Letters, vol. 12, 159, 1964.
R. Giri, "Temperature effect study upon the fluorescence emission of substituted coumarins," Spectrochimica Acta Part A: Molecular Spectroscopy, vol. 48, Issue 6, Jun. 1992, p. 843-848.
R. Sato, K. Kudo, T. Nagasawa, H. Suto, and K. Mizushima, "Simulations and Experiments Toward High-Data-Transfer-Rate Readers Composed of a Spin-Torque Oscillator," IEEE Transactions On Magnetics, vol. 48, 1758, 2012.
Rabehi, A., Electromagnetic microsystem for the detection of magnetic nanoparticles in a microfluidic structure for Immunoassays (Doctoral dissertation). Jan. 29, 2020.
Rauwerdink, A. M., Giustini, A. J., & Weaver, J. B. (2010). Simultaneous quantification of multiple magnetic nanoparticles. Nanotechnology, 21(45), 455101.
Riedinger, A., Guardia, P., Curcio, A., Garcia, M. A., Cingolani, R., Manna, L., & Pellegrino, T. (2013). Subnanometer local temperature probing and remotely controlled drug release based on azo-functionalized iron oxide nanoparticles. Nano letters, 13(6), 2399-2406.
S. Dutz and R. Hergt, "Magnetic nanoparticle heating and heat transfer on a microscale: Basic principles, realities and physical limitations of hyperthermia for tumour therapy," Int J Hyperthermia, 2013; 29(8): 790-800.
S.I. Kiselev et al., "Microwave oscillations of a nanomagnet driven by a spin-polarized current," Nature 425, pp. 380-383, 2003.
Srimani T. et al., "High Sensitivity Biosensor using Injection Locked Spin Torque Nano-Oscillators," arXiv: 1511.09072, Nov. 2015.
T. Nagasawa et al., "Delay detection of frequency modulation signal from a spin-torque oscillator under a nanosecond-pulsed magnetic field," Journal of Applied Physics, vol. 111, 07C908 (2012).
Tang, C., He, Z., Liu, H., Xu, Y., Huang, H., Yang, G., . . . & Chen, Z. (2020). Application of magnetic nanoparticles in nucleic acid detection. Journal of Nanobiotechnology, 18, 1-19. Apr. 21, 2020.
W. Andrä et al., "Temperature distribution as function of time around a small spherical heat source of local magnetic hyperthermia," Journal of Magnetism and Magnetic Materials, vol. 194, Issues 1-3, Apr. 1999, pp. 197-203.
Wang, W., & Jiang, Z., "Thermally assisted magnetic tunneling junction for biosensing applications," IEEE Transactions on Magnetics, 43(6), 2406-2408, Jun. 30, 2007.
Weifeng Shen et al., "Detection of DNA labeled with magnetic nanoparticles using MgO-based magnetic tunnel junction sensors," Journal of Applied Physics 103, 07A306 (2008).
Weijun Zhou, et al., "Novel dual fluorescence temperature-sensitive chameleon DNA-templated nanocluster pair for Intracellular thermometry" Nano Research (2018), vol. 11, pp. 2012-2023, Mar. 19, 2018, https://doi.org/10.1007/s12274-017-1817-7 Mar. 19, 2018 (Mar. 19, 2018).
Xia, Haiyan et al., "Micromagnetic simulation for detection of magnetic nanobeads by spin torque oscillator," Journal of Magnetism and Magnetic Materials 2017, vol. 432, pp. 387-390, Feb. 4, 2017.
Y.-C. Liang, L. Chang, W. Qiu, A. G. Kolhatkar, B. Vu, K. Kourentzi, T. R. Lee, Y. Zu, R. Willson, and D. Litvinov, "Ultrasensitive Magnetic Nanoparticle Detector for Biosensor Applications," Sensors, vol. 17, 1296, 2017.
Ye, F., Zhao, Y., El-Sayed, R., Muhammed, M., & Hassan, M. (2018). Advances in nanotechnology for cancer biomarkers. Nano Today, 18, 103-123.
Yu, L., Liu, J., Wu, K., Klein, T., Jiang, Y., & Wang, J. P. (2014). Evaluation of hyperthermia of magnetic nanoparticles by dehydrating DNA. Scientific reports, 4, 7216.
Extended European Search Report from European Application No. 20863334.7, dated Oct. 6, 2022.

| | A | G | T | C |
|---|---|---|---|---|
| Image 3/Range 3 | ● | | | ● |
| Image 2/Range 2 | | | ● | ● |
| Image 1/Range 1 | | | ● | ● |
| Result | A | G | T | C |

FIG. 2B

| | A | G | T | C |
|---|---|---|---|---|
| Image 2/Range 2 | ● | | | ● |
| Image 1/Range 1 | ● | | ● | |
| Result | A | G | T | C |

FIG. 2C

ENHANCED OPTICAL DETECTION FOR NUCLEIC ACID SEQUENCING USING THERMALLY-DEPENDENT FLUOROPHORE TAGS

CROSS-REFERENCE TO RELATED APPLICATIONS

This application is a continuation of, and hereby incorporates by reference in its entirety for all purposes the contents of, U.S. application Ser. No. 16/569,823, filed Sep. 13, 2019 and entitled "ENHANCED OPTICAL DETECTION FOR NUCLEIC ACID SEQUENCING USING THERMALLY-DEPENDENT FLUOROPHORE TAGS".

BACKGROUND

Deoxyribonucleic acid (DNA) is an example of a nucleic acid. DNA is a polymer or strand composed of only four possible constituent molecules or nucleotide bases (also referred to herein as simply "nucleotides"): adenine (A), cytosine (C), guanine (G), and thymine (T).

A DNA strand can be either single or double-stranded. Single-stranded DNA (ssDNA) can bind with its unique ssDNA complement to form a double-stranded version of itself (dsDNA). Adenine bases bond only with thymine bases, and cytosine bases bond only with guanine bases. For example, the sequence ACTGGC is complementary to and bonds with TGACCG. Because bases can occur in any order, the goal of DNA sequencing is to "read" a particular ssDNA strand or template, that is, to reliably determine the sequence of its bases.

One type of nucleic acid sequencing used for DNA sequencing is known as "sequencing by synthesis" (SBS). SBS involves binding of primer-hybridized template DNA, incorporation of a deoxynucleoside triphosphate (dNTP), and detection of incorporated dNTP. A ssDNA (i.e., a strand to be sequenced) is sequenced through an iterative buildup of its complement, with polymerase used to accelerate the rate of nucleotide incorporation. In one type of SBS, a long strand of DNA to be sequenced is cut into smaller strands, and these smaller strands can be sequenced at the same time, potentially after being "amplified" (i.e., copied) using a process such as bridge amplification, which is known in the art.

In one approach to SBS, the progress of the buildup of the complement of the bases of a DNA strand being sequenced is inferred through the detection of fluorescence. A fluorescent moiety is attached to each of the four dNTPs (A, T, C, and G). It is then possible to distinguish between the incorporation of different dNTPs into a growing nucleic acid strand because each of the fluorescent moieties excites and emits light at different wavelengths, which enables the target sequence to be determined. Typically, fluorescently-labeled dNTPs are excited and measured by one of four optical filters, one for each distinct dye, in a fluorescent sequencing instrument.

Such techniques may use fluorescence to generate an image using, e.g., an epifluorescence microscope or a confocal microscope. The specimen is illuminated with light of a specific wavelength (or wavelengths), which is absorbed by the fluorophores, thereby causing them to emit light of longer wavelengths (i.e., of a different color than the absorbed light). A spectral emission filter separates the illumination light from the weaker emitted fluorescence. A fluorescence microscope typically includes a light source (e.g., a laser), an excitation filter, a dichroic mirror (or beamsplitter), and an emission filter. The filters and the dichroic mirror/beamsplitter are chosen to match the spectral excitation and emission characteristics of the fluorophore used to label the specimen. The distribution of a single fluorophore (e.g., color, wavelength, etc.) is imaged at a time. Several single-color images must be combined to produce multi-color images of several types of fluorophores.

State-of-the-art sequencing systems that rely on fluorescence signal detection can provide throughputs of up to 20 billion reads per run. Achieving such performance, however, requires large-area flow cells, high-precision free-space imaging optics, and expensive high-power lasers to generate sufficient fluorescence signals to enable successful base detection.

There is, therefore, an ongoing need to improve nucleic acid sequencing technology.

SUMMARY

This summary represents non-limiting embodiments of the disclosure.

Disclosed herein are improvements to DNA sequencing in which fluorophores are used to tag dNTP types. The selected fluorophores emit light in a temperature-dependent manner over a range of temperatures between room temperature and an upper temperature (e.g., 100° C.). When the intensity of the emitted light is below the sensitivity threshold of the detectors used to capture the light, the fluorophores are not detected. Conversely, when the intensity of the emitted light is above the sensitivity threshold, the fluorophores are detected. By detecting the emitted intensity (or absence of emitted intensity exceeding a threshold) at multiple different temperatures (or within multiple distinct and non-overlapping temperature ranges) a determination of the dNTP incorporated at any given site can be determined with a reasonable number of (e.g., fewer than conventional fluorophore-based systems) chemistry steps without the more complicated optics necessary for existing systems.

In some embodiments, a method of sequencing nucleic acid uses a sequencing apparatus comprising a fluidic channel having a plurality of sites for attaching, to a surface of the fluidic channel, a plurality of nucleic acid strands to be sequenced. In some such embodiments, the method comprises, in one or more rounds of addition, adding, to the fluidic channel, (i) the plurality of nucleic acid strands, (ii) a plurality of molecules of nucleic acid polymerase, (iii) a first fluorescently-labeled nucleotide precursor comprising a first fluorescent label, and (iv) a second fluorescently-labeled nucleotide precursor comprising a second fluorescent label. An intensity of the first fluorescent label is greater than or equal to a first threshold in a first temperature range and in a second temperature range, the second temperature range being lower than the first temperature range, and an intensity of the second fluorescent label is less than or equal to a second threshold in the first temperature range and greater than or equal to the second threshold in the second temperature range. The method further comprises setting a temperature within the fluidic channel to be within the first temperature range, detecting a first intensity at each of the plurality of sites while the temperature of the fluidic channel is within the first temperature range, and in response to the first intensity at a particular site of the plurality of sites being greater than or equal to a first value, determining that the first fluorescently-labeled nucleotide precursor has been incorporated into the extendable primer at the particular site. The detected first intensity at the particular site may be zero or nonzero. The method further comprises setting the temperature within the fluidic channel to be within the second temperature range, detecting a second intensity at each of the plurality of sites while the temperature of the fluidic channel is within the second temperature range, and in response to the second intensity at the particular site being greater than or equal to a second value and the first intensity at the particular site being less than the first value, determining that the second fluorescently-labeled nucleotide precursor has been incorporated into the extendable primer at the particular site. The detected second intensity at the particular site may also be zero or nonzero.

In some embodiments, the first and second thresholds are approximately the same. In other embodiments, the first and second thresholds are different.

In some embodiments, the first and second values are approximately the same. In other embodiments, the first and second values are different.

In some embodiments, the first value is the first threshold, and the second value is the second threshold. In some embodiments, the first value is based on the first threshold, and the second value is based on the second threshold.

In some embodiments, the method further comprises adding, to the fluidic channel, a third fluorescently-labeled nucleotide precursor comprising a third fluorescent label, wherein an intensity of the third fluorescent label is less than a third threshold in the first and second temperature ranges and greater than or equal to the third threshold in a third temperature range, the third temperature range being lower than the second temperature range; setting the temperature within the fluidic channel to be within the third temperature range; detecting a third intensity (which may be zero or nonzero) at each of the plurality of sites while the temperature of the fluidic channel is within the third temperature range; and in response to the third intensity at the particular site being greater than or equal to a third value, and the first intensity at the particular site being less than the first value, and the second intensity at the particular site being less than the second value, determining that the third fluorescently-labeled nucleotide precursor has been incorporated into the extendable primer at the particular site.

In some such embodiments, the first, second, and third fluorescently-labeled nucleotide precursors are added to the fluidic channel at substantially the same time.

In some embodiments, the method further comprises, in response to the first intensity at the particular site being less than the first value, and the second intensity at the particular site being less than the second value, and the third intensity at the particular site being less than the third value, determining that a fourth, unlabeled precursor has been incorporated into the extendable primer at the particular site. In some such embodiments, at least two of the first, second, and third thresholds are approximately the same. In some embodiments, the first and second thresholds are different.

In some embodiments, at least two of the first, second, and third values are approximately the same. In some embodiments, the first, second, and third values are different.

In some embodiments, the method further comprises adding, to the fluidic channel, a fourth fluorescently-labeled nucleotide precursor comprising a fourth fluorescent label, wherein an intensity of the fourth fluorescent label is less than a fourth threshold in each of the first, second, and third temperature ranges and greater than or equal to the fourth threshold in a fourth temperature range, the fourth temperature range being lower than the third temperature range; setting the temperature within the fluidic channel to be within the fourth temperature range; detecting a fourth intensity (which may be zero or non zero) at each of the plurality of sites while the temperature of the fluidic channel is within the fourth temperature range; and in response to the fourth intensity at the particular site being greater than or equal to a fourth value, and the first intensity at the particular site being less than the first value, and the second intensity at the particular site being less than the second value, and the third intensity at the particular site being less than the third value, determining that the fourth fluorescently-labeled nucleotide precursor has been incorporated into the extendable primer at the particular site.

In some such embodiments, two or more of the first, second, third, and fourth thresholds are approximately the same.

In some embodiments, two or more of the first, second, third, and fourth values are approximately the same.

In some embodiments, the first, second, third, and fourth fluorescently-labeled nucleotide precursors are added to the fluidic channel at substantially the same time.

In some embodiments, a method of sequencing nucleic acid using a sequencing apparatus comprising a fluidic channel having a plurality of sites for attaching, to a surface of the fluidic channel, a plurality of nucleic acid strands to be sequenced, comprises: in one or more rounds of addition, adding, to the fluidic channel, (i) the plurality of nucleic acid strands, (ii) a plurality of molecules of nucleic acid polymerase, (iii) a first fluorescently-labeled nucleotide precursor comprising a first fluorescent label, wherein an intensity of the first fluorescent label is less than a first threshold in a first temperature range and greater than or equal to the first threshold in a second temperature range, the second temperature range being lower than the first temperature range, (iv) a second fluorescently-labeled nucleotide precursor comprising a second fluorescent label, wherein an intensity of the second fluorescent label is greater than or equal to a second threshold in the first temperature range and in the second temperature range, and (v) a third fluorescently-labeled nucleotide precursor comprising the first and second fluorescent labels; setting a temperature within the fluidic channel to be within the first temperature range; detecting a first intensity (which may be zero or nonzero) at each of the plurality of sites while the temperature of the fluidic channel is within the first temperature range; setting the temperature within the fluidic channel to be within the second temperature range; detecting a second intensity (which may be zero or nonzero) at each of the plurality of sites while the temperature of the fluidic channel is within the second temperature range; and determining whether one of the first, second, or third fluorescently-labeled nucleotide precursors has been incorporated into the extendable primer at a particular site of the plurality of sites.

In some such embodiments, the first, second, and third fluorescently-labeled nucleotide precursors are added to the fluidic channel at substantially the same time.

In some embodiments, determining whether one of the first, second, or third fluorescently-labeled nucleotide precursors has been incorporated into the extendable primer at the particular site of the plurality of sites comprises: in response to the first intensity at the particular site being less than a first value, and the second intensity at the particular site being greater than or equal to a second value, determining that the first fluorescently-labeled nucleotide precursor has been incorporated into the extendable primer at the particular site; in response to the first intensity at the particular site being greater than or equal to the first value, and the second intensity at the particular site being greater than or equal to a third value, the third value being greater than each of the first and second values, determining that the third fluorescently-labeled nucleotide precursor has been incorporated into the extendable primer at the particular site; and in response to the first intensity at the particular site being greater than or equal to the first value, and the second intensity at the particular site being greater than or equal to the second value and less than the third value, determining that the second fluorescently-labeled nucleotide precursor has been incorporated into the extendable primer at the particular site.

In some such embodiments, the method further comprises, in response to the first intensity at the particular site being less than the first value, and the second intensity at the particular site being less than the second value, determining that a fourth, unlabeled nucleotide precursor has been incorporated into the extendable primer at the particular site.

In some embodiments, the method further comprises determining that none of the first, second, or third fluorescently-labeled nucleotide precursors has been incorporated into the extendable primer at the particular site, and, in response to determining that none of the first, second, or third fluorescently-labeled nucleotide precursors has been incorporated into the extendable primer at the particular site, inferring that a fourth, unlabeled nucleotide precursor has been incorporated into the extendable primer at the particular site.

In some embodiments, the first and second thresholds are approximately the same. In other embodiments, the first and second thresholds are different.

In some embodiments, the first and second values are substantially the same. In other embodiments, the first and second values are different.

In some embodiments, the third value is approximately or exactly the sum of the first and second values.

In some embodiments, the first value is the first threshold, and the second value is the second threshold.

In some embodiments, the first value is based on the first threshold, and the second value is based on the second threshold.

In some embodiments, the third value is approximately the sum of the first and second values.

In some embodiments, a system for sequencing nucleic acid comprises a fluidic channel, a heater coupled to the fluidic channel, an imaging system, and at least one processor. In some embodiments, the fluidic channel has a plurality of sites for attaching, to a surface of the fluidic channel, a plurality of nucleic acid strands to be sequenced. In some embodiments, the heater is configured to set a temperature of a contents of the fluidic channel to be within any of nonoverlapping first, second, third, and fourth temperature ranges. In some embodiments, the imaging system is configured to detect an intensity at each of the plurality of sites in each of the first, second, third, and fourth temperature ranges. In some embodiments, the second temperature range is lower than the first temperature range, the third temperature range is lower than the second temperature range, and the fourth temperature range is lower than the third temperature range.

The at least one processor is configured to execute at least one machine-readable instruction. In some embodiments, when executed, the at least one machine-executable instruction causes the at least one processor to identify a first fluorescently-labeled nucleotide precursor or a complementary base of the first fluorescently-labeled nucleotide precursor in response to an intensity at a particular site of the plurality of sites being greater than or equal to a first threshold in the first temperature range and in the second temperature range. In some embodiments, when executed, the at least one machine-executable instruction causes the at least one processor to identify a second fluorescently-labeled nucleotide precursor or a complementary base of the second fluorescently-labeled nucleotide precursor in response to the intensity at the particular site of the plurality of sites being less than a second threshold in the first temperature range and greater than or equal to the second threshold in the second temperature range. In some embodiments, when executed, the at least one machine-executable instruction causes the at least one processor to identify a third fluorescently-labeled nucleotide precursor or a complementary base of the third fluorescently-labeled nucleotide precursor in response to the intensity at the particular site of the plurality of sites being less than a third threshold in the first and second temperature ranges and greater than or equal to the third threshold in the third temperature range. In some embodiments, when executed, the at least one machine-executable instruction causes the at least one processor to identify a fourth fluorescently-labeled nucleotide precursor or a complementary base of the fourth fluorescently-labeled nucleotide precursor in response to the intensity at the particular site of the plurality of sites being less than a fourth threshold in each of the first, second, and third temperature ranges and greater than or equal to a fourth threshold in the fourth temperature range.

In some embodiments, the fluidic channel comprises a structure (e.g., a cavity, a ridge, etc.) that includes the plurality of sites for attaching, to the surface of the fluidic channel, the plurality of nucleic acid strands to be sequenced.

In some embodiments, the heater comprises a thermal sensor or a microprocessor.

In some embodiments, the imaging system comprises a camera, a light source (e.g., a laser), illumination optics, a detector, an optical blocking filter, an analog-to-digital converter (ADC), or one or more sensors. The illumination optics may be configured to distribute the excitation light substantially uniformly over the plurality of sites. In some embodiments, the detector comprises a lens. In some such embodiments, the imaging system includes an optical blocking filter that is situated within the system such that it substantially isolates the lens from light emitted by the light source. In some embodiments, the one or more sensors of the imaging system comprise a charge-coupled device (CCD) sensor.

In some embodiments, when executed by the at least one processor, the at least one machine-readable instruction further causes the at least one processor to control the heater, the imaging system, or both.

In some embodiments, a system for sequencing nucleic acid comprises a fluidic channel, a heater coupled to the fluidic channel, an imaging system, and at least one processor. In some embodiments, the fluidic channel has a plurality of sites for attaching, to a surface of the fluidic channel, a plurality of nucleic acid strands to be sequenced. In some embodiments, the heater is configured to set a temperature of a contents of the fluidic channel to be within either of first and second temperature ranges, wherein the first and second temperature ranges are nonoverlapping. In some embodiments, the imaging system is configured to detect an intensity at each of the plurality of sites in each of the first and second temperature ranges.

The at least one processor is configured to execute at least one machine-readable instruction. In some embodiments, when executed, the at least one machine-executable instruction causes the at least one processor to instruct the heater to set a temperature within the fluidic channel to be within the first temperature range and obtain, from the imaging system, an indication of a first intensity at each of the plurality of sites while the temperature of the fluidic channel is within the first temperature range. In some embodiments, when executed, the at least one machine-executable instruction further causes the at least one processor to instruct the heater to set the temperature within the fluidic channel to be within the second temperature range and obtain, from the imaging system, an indication of a second intensity at each of the plurality of sites while the temperature of the fluidic channel is within the second temperature range. In some embodiments, when executed, the at least one machine-executable instruction further causes the at least one processor to determine that a first fluorescently-labeled nucleotide precursor has been incorporated into an extendable primer at the particular site in response to the first intensity at a particular site of the plurality of sites being less than a first value, and the second intensity at the particular site being greater than or equal to a second value. In some embodiments, when executed, the at least one machine-executable instruction further causes the at least one processor to determine that a second fluorescently-labeled nucleotide precursor has been incorporated into the extendable primer at the particular site in response to the first intensity at the particular site being greater than or equal to the first value, and the second intensity at the particular site being greater than or equal to the second value and less than a third value, the third value being greater than each of the first and second values. In some embodiments, when executed, the at least one machine-executable instruction further causes the at least one processor to determine that a third fluorescently-labeled nucleotide precursor has been incorporated into the extendable primer at the particular site in response to the first intensity at the particular site being greater than or equal to the first value, and the second intensity at the particular site being greater than or equal to the third value.

BRIEF DESCRIPTION OF THE DRAWINGS

Objects, features, and advantages of the disclosure will be readily apparent from the following description of certain embodiments taken in conjunction with the accompanying drawings in which:

FIG. 2B illustrates conceptually the use of three intensity-measuring events, three temperature ranges, and three fluorescently-labeled nucleotide precursors, each having a different fluorescent label, in accordance with some embodiments.

FIG. 2C illustrates conceptually the use of two intensity-measuring events, two temperature ranges, and two fluorescently-labeled nucleotide precursors, each having a different fluorescent label, in accordance with some embodiments.

DETAILED DESCRIPTION

Figure 1A:
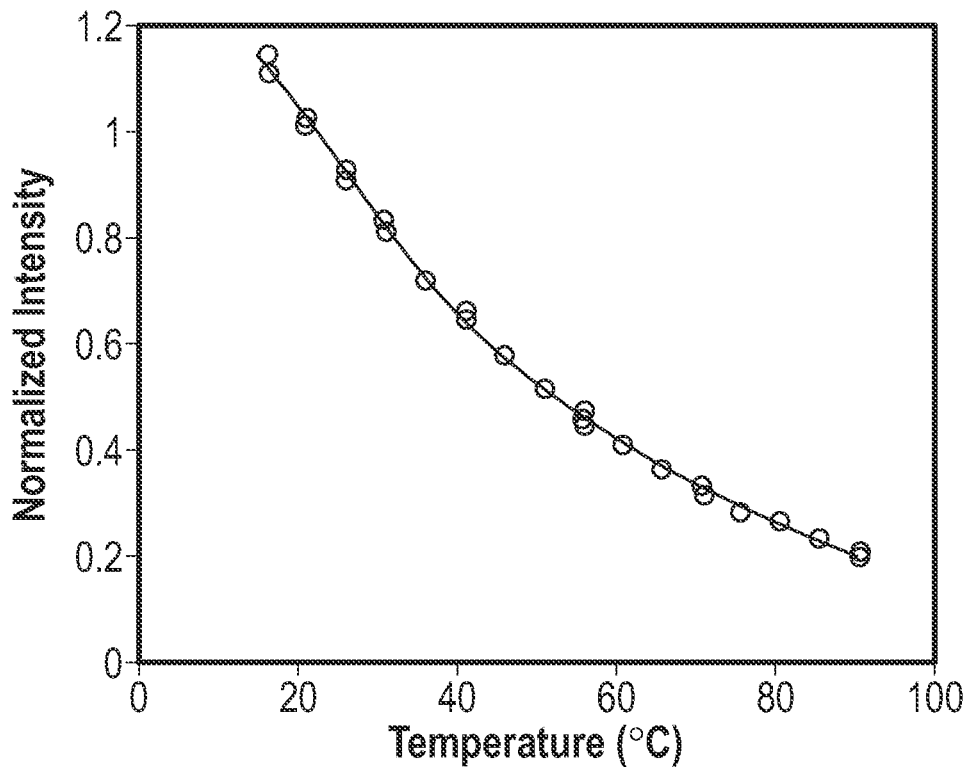
FIG. 1A illustrates the temperature dependence of the fluorescent intensity of a fluorescent dye.

The term "nucleotide" as used herein includes both deoxyribonucleotides and ribonucleotides, as well as modified nucleotides such as dideoxynucleotides and other chain terminator nucleotides. It also includes nucleotide residues within a polynucleotide. The terms "nucleotide" and "base" are used interchangeably herein.

The term "fluorescent dye" as used herein refers to a dye whose presence can be detected by fluorescence. In particular embodiments, the fluorescent dyes used herein are suitable for nucleic acid sequencing.

The term "nucleic acid polymerase" includes DNA polymerases and RNA polymerases. The DNA polymerases can be DNA-dependent or RNA-dependent (i.e., reverse transcriptase). DNA polymerases include, for example, Taq DNA polymerase (*Thermus aquaticus* DNA polymerase), mutant forms of Taq DNA polymerase, such as Taq G46D F667Y DNA polymerase, and others known in the art.

The term "nucleic acid substrate" as used herein refers to a nucleic acid that is modified by a chemical or enzymatic reaction, or to a nucleic acid that serves as a template for a chemical or enzymatic reaction. For instance, in a nucleic acid sequencing reaction, both the oligonucleotide that is extended by a polymerase and the template nucleic acid are "nucleic acid substrate," as the term is used herein.

As used herein, the term "chain terminator nucleotide" refers to a mononucleotide that can be incorporated into a growing polynucleotide chain by a nucleic acid polymerase and that when incorporated terminates the chain because a polynucleotide containing the chain terminator nucleotide at its 3' terminus cannot serve as a substrate for the addition of another nucleotide by the nucleic acid polymerase. Typical terminators are those in which the nucleobase is a purine, a 7-deaza-purine, a pyrimidine, a normal nucleobase or a common analog thereof and the sugar moiety is a pentose that includes a 3'-substituent that blocks further synthesis, such as a dideoxynucleotide (ddNTP). Examples of ddNTPs are ddGTP, ddATP, ddTTP, and ddCTP. Substituents that block further synthesis include, but are not limited to, amino, deoxy, halogen, alkoxy and aryloxy groups. Exemplary terminators include, but are not limited to, those in which the sugar-phosphate ester moiety is 3'-($C_1$-$C_6$)alkylribose-5'-triphosphate, 2'-deoxy-3'-($C_1$-$C_6$)alkylribose-5'-triphosphate, 2'-deoxy-3'-($C_1$-$C_6$)alkoxyribose-5'-triphosphate, 2'-deoxy-3'-($C_5$-$C_{14}$)aryloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate.

Existing fluorescence-based technologies used to differentiate between different bases in a sample (e.g., in fluorescence-based nucleic acid sequencing technologies) rely on, for example, the quality of a signal generated by a detection moiety that is associated with a particular type of nucleotide. For example, traditional fluorescent sequencing technologies utilize identifiably distinct fluorescent moieties, each attached to one of the four nucleotides A, T, C, and G that are utilized in a sequencing reaction.

One conventional method of DNA sequencing involves adapting ssDNA for attachment to a solid support of a sequencing apparatus and amplifying the quantity of the ssDNA using techniques such as the polymerase chain reaction to create many DNA molecules with a short leader. An oligo complementary to the short leader may then be added so that there is a short section of dsDNA at the leader. The double stranded portion of the bound molecule is a primer for a suitable DNA polymerase, such as, for example, Taq polymerase, which is operable at high temperatures.

The sequencing can then take one of several approaches. For example, the sequencing can use a mixture of four fluorescently-labeled 3'-blocked NTPs (fluorescently labeled dideoxynucleotide terminators), where the fluorescent label is part of the 3'-blocking group. The fluorescent label serves as a "reversible terminator" for polymerization. Each of the NTPs is labeled by a different label (i.e., each of the A, G, C, and T nucleotides has a different label), and the different labels are distinguishable by fluorescent spectroscopy or by other optical means.

Four fluorescently-labeled nucleotide precursors can be used to sequence millions of clusters of DNA strands in parallel. DNA polymerase catalyzes the incorporation of fluorescently-labeled dNTPs into a DNA template strand during sequential cycles of DNA synthesis. In each sequencing cycle, the bound double strand DNA molecule is exposed to DNA polymerase and a mixture of the four fluorescently-labeled 3'-blocked NTPs. The polymerase adds one of the four dNTPs to the growing oligonucleotide chain (i.e., whichever dNTP is complementary to the next unpaired base in the ssDNA). The unincorporated dNTPs and other impurities that are either left unreacted or generated during the reactions are then separated from the vicinity of the support-bound DNA by washing at a temperature that prevents the free dNTPs from binding to the ssDNA but is not so high as to dehybridize the dsDNA.

Because only one of the four types of dNTP will have been added to the oligonucleotide, and the four fluorescent labels are distinguishable, the identity of the incorporated dNTP can be identified through laser excitation and imaging. Specifically, each of four filters is used to determine whether light of a particular wavelength (e.g., color) is emitted. The fluorescent label can then be enzymatically cleaved to allow the next round of incorporation. Because each base type can pair with one and only one other base type, the identity of the just-paired base in the unknown sequence of the ssDNA is known from the identity of the incorporated dNTP (which is known from the wavelength of emitted light). Thus, the base is identified directly from fluorescence measurements during each cycle.

One disadvantage of the above-described approach is that a complicated optics system is needed to filter out different wavelengths of light to detect the fluorescent labels of the incorporated dNTPs and to distinguish between the different emitted colors. Other approaches have been developed to simplify the optics system, but they are slower to sequence and require intermediate chemistry steps within each sequencing cycle. Thus, these approaches have been introduced in smaller, less expensive entry-level sequencing systems but not in higher-level systems requiring fast throughput.

Disclosed herein are improved methods of sequencing nucleic acid. The inventors had the insight that some fluorescent dyes emit light at an intensity that varies with temperature, and this temperature-dependence of the emitted intensity can be exploited for nucleic acid sequencing applications. The disclosed methods enable the use of simpler optics systems than the conventional four-dye approach described above because they do not require wavelength filtering. Instead, the temperature of the system is adjusted during each sequencing cycle (e.g., by using an integrated heating element of the sequencing device). Furthermore, all four bases may be introduced in a single step. The emission, or lack of emission, of light by the fluorescent dyes at different temperatures (or within different temperature ranges) can be used to detect the fluorescent labels of the incorporated dNTPs and thereby sequence the nucleic acid. For instance, and as will be described in further detail below in the context of some embodiments, in a composition containing four chain terminator nucleotides, each linked to a different fluorescent dye, each of the four fluorescent dyes will emit light in a temperature-dependent manner such that it is distinguishable from the other dyes.

The temperature response of fluorescent dyes has been used to perform microscale local temperature measurements of microfluidic and biological systems. Some such systems are described in the 2001 paper entitled "Temperature Measurement in Microfluidic Systems Using a Temperature-Dependent Fluorescent Dye" by D. Ross, M. Gaitan, and L. Locasco (Analytical Chemistry, Vol. 73, No. 17, Sep. 1, 2001). FIG. 1A herein illustrates the temperature dependence of the fluorescence intensity of one such fluorescent dye, namely Rhodamine B. As shown in FIG. 1A, the intensity decreases monotonically as the temperature increases. Above room temperature (assumed to be 20 degrees Celsius), the intensity of emitted light decreases rapidly. Thus, if a detector in a nucleic acid sequencing apparatus were to have a detection threshold of, for example 80% of the peak intensity, it would detect the dye at temperatures below about 32 degrees Celsius but not above that temperature.

Figure 1B:
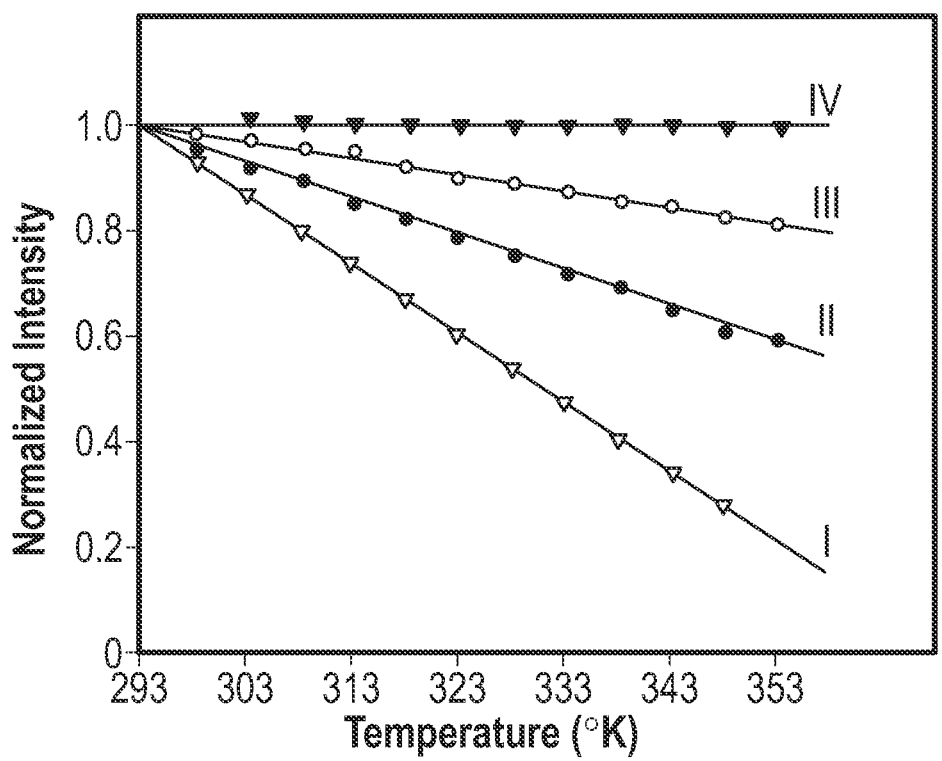
FIG. 1B illustrates the temperature dependence of the fluorescent intensities of additional fluorescent dyes.

For comparison, FIG. 1B illustrates the temperature dependence of the fluorescent intensities of various coumarin dyes, namely 4-methyl-7-methoxy (labeled "I" in FIG. 1B), 4-methyl-5,7-diethoxy (labeled "II"), 4-methyl-5-ethoxy-7-methoxy (labeled "III"), and 4-methyl-7,8-diethoxy (labeled "IV"). (See, e.g., R. Giri, "Temperature effect study upon the fluorescence emission of substituted coumarins," Spectrochimica Acta Part A: Molecular Spectroscopy, Volume 48, Issue 6, June 1992, p. 843-848.) As FIG. 1B shows, the intensity of 4-methyl-7,8-diethoxy (IV) is relatively insensitive to temperature. In contrast, the intensity of 4-methyl-7-methoxy (I) decreases rapidly with increasing temperature.

Thus, the inventors had the insight that the intensity response can be exploited so that two different fluorescent labels with different responses to changes in temperature can be used to distinguish between two nucleotides in nucleic acid sequencing. For example, a comparison of the temperature responses of Rhodamine (FIG. 1A) and coumarin (III) (FIG. 1B) indicates that at 50 degrees Celsius, the intensity of Rhodamine is half of its value at room temperature, whereas the intensity of coumarin (III) is ninety percent of its value at room temperature. Assuming the intensities of Rhodamine and coumarin (III) are approximately the same at room temperature, by tuning a photodetector to have a minimum sensitivity for light intensity set to a value between 50% and 90% (e.g., 75%), the photodetector would detect light from both dyes at room temperature but only for coumarin (III) at 50 degrees Celsius. One advantage of this approach relative to conventional approaches to nucleic acid sequencing is that there is no need to filter the wavelength of emitted light or determine the color of light emitted by the dye; knowledge of the temperature-dependence of the intensity of light emitted by the dye when excited into fluorescence allows the different dyes to be distinguished. Therefore, the need for the complexities and expense associated with a need to have optical filters is reduced or eliminated altogether.

It is to be understood that the intensity profiles of the selected dyes need not be monotonic, smooth, or linear. It is contemplated that the selected dyes may have predictable emitted intensities in some temperature ranges and unpredictable (or nonlinear, random, etc.) emitted intensities in other ranges.

Figure 1C:
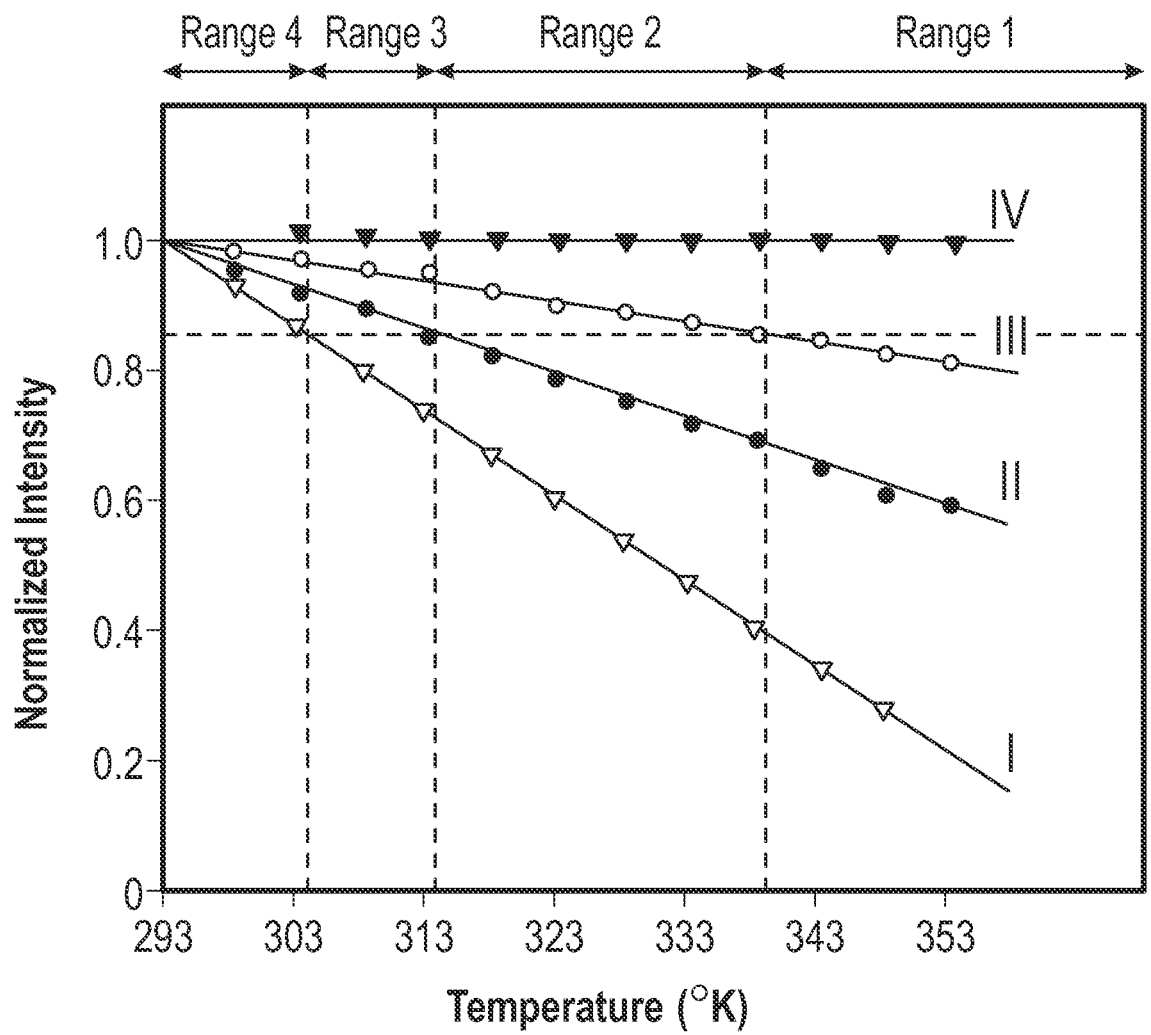
FIG. 1C is an annotated version of FIG. 1B showing how the temperature dependence of the emissions of the four fluorescent dyes can be exploited for nucleic acid sequencing.

FIG. 1C is an annotated version of FIG. 1B to illustrate how the temperature-dependence of different fluorescent dyes can be used to distinguish between the dyes. It is to be understood that FIGS. 1B and 1C show the normalized intensities of the four fluorescent dyes. Thus, this explanation assumes that the peak intensity of light emitted by each of the fluorescent dyes at room temperature (approximately 273 degrees Kelvin if 20 degrees Celsius is room temperature) is approximately the same.

As shown in FIG. 1C, a threshold of approximately 85% intensity has been selected as an example. In the highest temperature range, labeled "Range 1," only the dye IV emits light at an intensity that meets or exceeds the threshold. In the next-highest temperature range, labeled "Range 2," only the dyes III and IV emit light at an intensity that meets or exceeds the threshold. In the next-highest temperature range, labeled "Range 3," lowest temperature range, only the dyes II, III, and IV emit light at an intensity that meets or exceeds the threshold. Finally, in the lowest temperature range, labeled "Range 4," all four of the fluorescent dyes emit light at an intensity that meets or exceeds the threshold.

Continuing with the example shown in FIG. 1C, in a DNA sequencing application, each of the four nucleotides can be labeled with a different one of the four fluorescent dyes shown. For example, A can be labeled using dye I, G can be labeled using dye II, T can be labeled using dye III, and C can be labeled using dye IV. When the temperature is within Range 1, only dye IV will emit light at an intensity that meets or exceeds the threshold. Thus, if, in the temperature Range 1, light is detected at or above the threshold, the incorporated base must be cytosine (C). On the other hand, if, in the temperature Range 1, no light is detected at or above the threshold, the incorporated base is not cytosine (C). An image may be taken in each of the four temperature ranges to record the detected light (or absence of detected light). As used herein, the term "image" refers to any record of the presence or absence of emitted light (e.g., an optical response over a plurality of physical locations). For example, an image may be, literally, an image of a sequencing apparatus's fluidic channel, recorded using a camera, potentially using a filter to detect light of a particular wavelength at particular physical locations where nucleic acid strands (or portions of strands) are attached or bound. As another example, an image may be a data file recording the detected intensity of emitted light (e.g., in candelas, lumens or any other suitable units) at various physical locations where nucleic acid is attached or bound. As yet another example, an image may be a data file recording whether or not light was detected at a particular location where nucleic acid is attached or bound (e.g., a 1 if light exceeding a threshold was detected, a 0 if light exceeding the threshold was not detected). Whatever its form, an image may be stored temporarily or permanently (e.g., so its contents may be compared to other images), or it may be transient (e.g., created and compared in real time to a previously-created-and-stored image).

When the temperature is within Range 2, only dyes III (T) and IV (C) will emit light at an intensity that meets or exceeds the threshold. Thus, if, in the temperature Range 2, light is detected at or above the threshold, the incorporated base is not adenine (A) or guanine (G). Based on knowledge of whether light above the threshold is detected when the temperature is within Range 1, it can be determined whether the incorporated base is cytosine (C) (light detected in Range 1 and Range 2) or thymine (T) (no light detected in Range 1, light detected in Range 2).

When the temperature is within Range 3, all of the dyes except for dye I will emit light at an intensity above a threshold. Thus, if in the temperature Range 3, light is detected at or above the threshold, it can be concluded that the incorporated base is not adenine (A). Based on knowledge of whether light above the threshold is detected when the temperature is within Range 1, within Range 2, and within Range 3 it can be determined whether the incorporated base is cytosine (C) (light detected in Ranges, 1, 2, and 3), thymine (T) (no light detected in Range 1, but light detected in Ranges 2 and 3) or guanine (G) (no light detected in Ranges 1 and 2, but light detected in Range 3).

When the temperature is within Range 4, all of the dyes will emit light at or above a threshold. Based on an assessment of the detection of light (or absence of light) in each of the four temperature ranges, it can be determined which nucleotide has been incorporated in the sequencing step. Specifically, the nucleotide is cytosine (C) if light is detected in all four temperature ranges; the nucleotide is thymine (T) if light is detected only in Ranges 2, 3, and 4; the nucleotide is guanine (G) if light is detected only in Ranges 3 and 4; and the nucleotide is adenine (A) if light is detected only in Range 4.

As this example illustrates, by manipulating the temperature during each sequencing step (i.e., setting the temperature to different values during a sequencing cycle and detecting the presence or absence of emitted light at or above a threshold), the different incorporated bases can be distinguished from one another. The temperature ranges can be tested in any order. It will be appreciated that when it is desirable to determine whether and which base has been incorporated in a particular strand of nucleic acid being sequenced, beginning in Range 1 may be advantageous because if light is detected in Range 1 during a cycle, it can be concluded that the incorporated nucleotide is cytosine (C). Thus, there is no need to check Ranges 2, 3 or 4 if emitted light at or above a threshold is detected in Range 1. It will also be appreciated that testing in Range 3 first may be advantageous because if no light is detected in Range 3, it can be concluded that the incorporated nucleotide is adenine (A). Thus, there is no need to check Ranges 1, 2, or 4.

As described previously, in some types of SBS, a long strand of DNA is (or a plurality of long strands of DNA from a single donor organism are) cut into smaller, random-length segments prior to sequencing. All of these smaller strands, which are from the same donor, are randomized sub-strands of the complete strand to be sequenced. For example, if the complete strand includes the sequence ATGGCTTAG, the smaller strands could include, for example, distinct sub-strands (e.g., ATGG and TTAG) as well as, if a plurality of the longer strands are cut into sub-strands, sub-strands that partially or completely overlap other sub-strands (e.g., GGCTT and ATGGCT). All of the smaller, randomized sub-strands may be sequenced at the same time, potentially after being amplified. In such applications, it will be appreciated that because the sub-strands do not represent the same sub-sequences, it is desirable to determine the intensity in each of the temperature ranges because the sequencing of the sub-strands will not be coordinated (or synchronized) amongst sub-strands. For example, during a single sequencing cycle, a first sub-strand may incorporate cytosine, a second sub-strand might incorporate thymine, and a third sub-strand might incorporate adenine. In order to sequence multiple random segments of a larger nucleic acid strand, it is desirable, in each sequencing cycle, to determine whether and at which physical location(s) each dNTP has been incorporated.

As will be understood by those having skill in the art in view of the disclosures herein, the same general procedure as described in the context of FIG. 1C can be used if the peak intensities of the different dyes differ. In such cases, the intensity threshold applicable within the different temperature ranges may differ, and the appropriate values may be determined based on knowledge of the temperature-dependent characteristics of each of the fluorescent dyes.

Figure 2A:
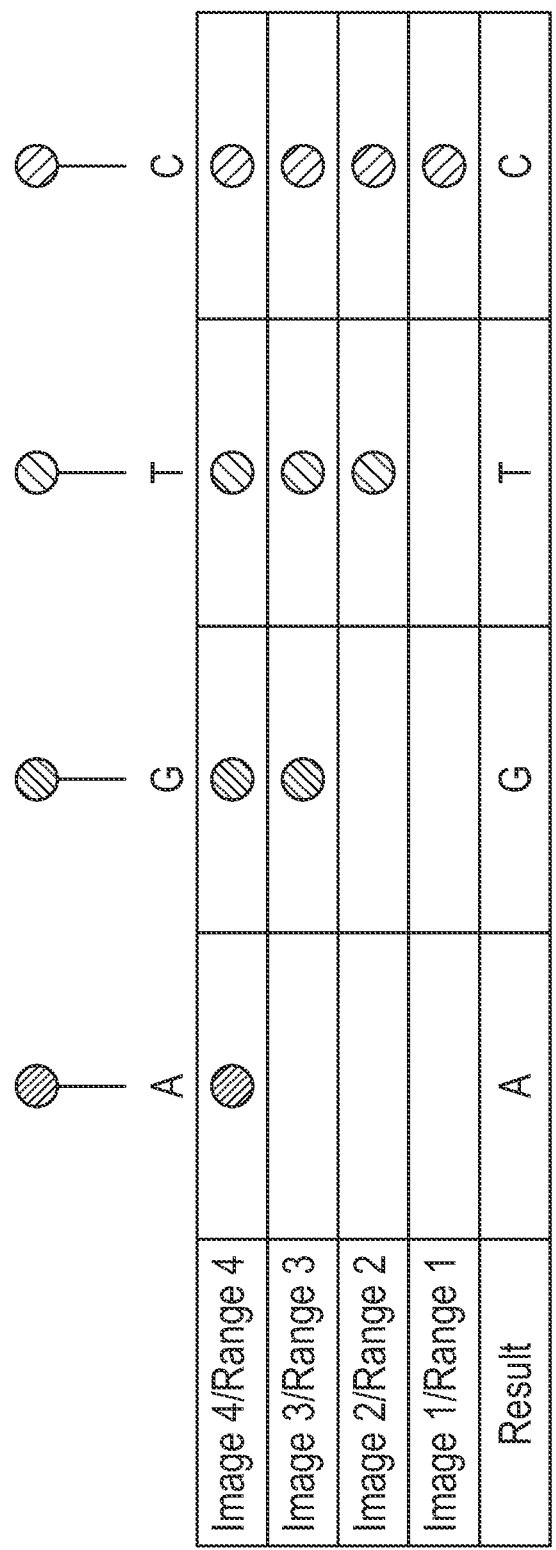
FIG. 2A illustrates the use of four intensity-measuring events, four temperature ranges, and four fluorescently-labeled nucleotide precursors for nucleic acid sequencing in accordance with some embodiments.

FIGS. 2A through 2C illustrate how the different incorporated nucleotides can be identified using these principles in accordance with some embodiments. Each of the four nucleotides can be labeled with a different dye, each dye having a different fluorescence intensity dependence on temperature. The colors of the dyes are immaterial, as long as the temperature at which the intensity of the fluorescence drops below a threshold is different for each dye.

FIG. 2A illustrates conceptually the use of four images, four temperature ranges, and four fluorescently-labeled nucleotide precursors, each having a different fluorescent label (which may be cleavable), in accordance with some embodiments. FIG. 2A is effectively a logic table that can be applied individually to determine, for each nucleic acid strand or sub-strand, which nucleotide has been incorporated into that strand or sub-strand. For example, if the fluorescent dyes, threshold, and temperature ranges shown in FIG. 1C are assumed, A is labeled using dye I, G is labeled using dye II, T is labeled using dye III, and C is labeled using dye IV. Following incorporation of a nucleotide into a growing nucleic acid chain, the temperature of the reaction is set to be within one of the temperature ranges. For purposes of this explanation, assume that the testing proceeds from the highest temperature to the lowest temperature. As explained above, this order is arbitrary, and the temperature ranges can be tested in any order. Moreover, depending on the results obtained when the temperature is within a particular range, it may be unnecessary in a sequencing cycle to test more than one temperature range. As explained above, when randomized sub-strands are sequenced at the same time, it will be appreciated that because the sub-strands do not represent the same sub-sequences, it is desirable to determine the intensity in each of the temperature ranges because the sequencing of the sub-strands will not be coordinated (or synchronized) amongst sub-strands.

After the temperature is set to be within Range 1, which, in this example, is assumed to be the highest of the four temperature ranges, the reaction is then exposed to light, and fluorescence is observed and recorded as Image 1; this constitutes a first imaging event and a first fluorescence detection pattern. The temperature is then decreased to be within Range 2. The reaction location is once again illuminated and the fluorescence is captured and recorded as Image 2, constituting a second imaging event (i.e., a second fluorescence detection pattern). The temperature is then decreased to be within Range 3. The reaction location is once again illuminated and the fluorescence is captured and recorded as Image 3, constituting a third imaging event (i.e., a third fluorescence detection pattern). The temperature is then decreased to be within Range 4. The reaction location is once again illuminated and any change in fluorescence is captured and recorded, constituting a fourth imaging event (i.e., a fourth fluorescence detection pattern).

As denoted in FIG. 2A, Image 1 is taken when the temperature is within Range 1, Image 2 is taken when the temperature is within Range 2, Image 3 is taken when the temperature is within Range 3, and Image 4 is taken when the temperature is within Range 4. Within the temperature Range 4, all four dyes emit light at an intensity greater than the threshold, as shown in FIG. 2A, and therefore it is not possible to determine from Image 4 alone which of the four fluorescently-labeled nucleotide precursors has been incorporated into the extendible primer. Within the temperature Range 3, however, only the fluorescent dyes labeling G, T, and C will emit light at an intensity greater than the threshold. Therefore, based on the presence of emitted light of greater-than-threshold intensity in Image 4 and the absence of emitted light at or above a threshold in Image 3, one can determine that the incorporated nucleotide precursor is A. Similarly, only the fluorescent dyes labeling T and C will emit light at an intensity greater than the threshold within the temperature Range 2. Therefore, based on the presence of emitted light of greater-than-threshold intensity in Images 4 and 3 and the absence of emitted light at or above a threshold in Image 2, one can determine that the incorporated nucleotide precursor is G. Similarly, only the fluorescent dye labeling C will emit light at an intensity greater than the threshold within the temperature Range 1. Therefore, based on the presence of emitted light of greater-than-threshold intensity in Images 4, 3, and 2 and the absence of emitted light at or above a threshold in Image 1, one can determine that the incorporated nucleotide precursor is T. And, of course, if the detected intensity exceeds the threshold in all four of the images, it can be determined that the incorporated nucleotide precursor is C.

Because all four of the fluorescently-labeled nucleotide precursors emit light at an intensity meeting or exceeding the threshold in the temperature Range 4, it is possible to simplify the procedure by eliminating imaging in temperature Range 4. FIG. 2B illustrates conceptually the use of three images, three temperature ranges, and three fluorescently-labeled nucleotide precursors, each having a different fluorescent label, in accordance with some embodiments. Like FIG. 2A, FIG. 2B is effectively a logic table that can be applied individually to determine, for each nucleic acid strand or sub-strand, which nucleotide has been incorporated into that strand or sub-strand. The fourth nucleotide precursor (shown as guanine (G) in FIG. 2B) is unlabeled. In this approach, Image 1 is taken while the temperature is in Range 1, Image 2 is taken while the temperature is in Range 2, and Image 3 is taken while the temperature is in Range 3.

The fluorescent dye labeling cytosine (C) is the only dye that will emit light at an intensity greater than or equal to the threshold within temperature Range 1. Thus, if the detected intensity in Image 1 is greater than or equal to the threshold, it can be determined that the incorporated nucleotide precursor is cytosine (C). Otherwise, Image 2 can be used to determine whether the incorporated nucleotide precursor is T: because only the fluorescent dyes labeling thymine (T) and cytosine (C) will emit light at an intensity greater than the threshold within the temperature Range 2, the presence of emitted light of greater-than-threshold intensity in Image 2 and less-than-threshold intensity in Image 1 indicates that the incorporated nucleotide precursor is thymine (T). Similarly, the fluorescent dye labeling adenine (A) will emit light at an intensity greater than the threshold only within Range 3. Therefore, based on the presence of emitted light of greater-than-threshold intensity in Image 3, but not in Image 2 or Image 1, one can determine that the incorporated nucleotide precursor is adenine (A). If emitted light of greater-than-threshold intensity is not detected in any of Images 1, 2, or 3, it can be concluded (e.g., inferred) that the incorporated nucleotide is guanine (G).

FIG. 2C illustrates an alternative embodiment in which only two images are used to determine which of the four nucleotide precursors has been incorporated, in accordance with some embodiments. This embodiment uses a photodetector that is intensity-sensitive above its intensity threshold, which means it not only detects that emitted light is present but also detects the intensity of the emitted light. Similarly to FIGS. 2A and 2B, FIG. 2C is effectively a logic table that can be applied individually to determine, for each nucleic acid strand or sub-strand, which nucleotide has been incorporated into that strand or sub-strand. One nucleotide (shown as T in FIG. 2C) is labeled with a first dye, and a second nucleotide (shown as C in FIG. 2C) is labeled with a second dye. One nucleotide (shown as A in FIG. 2C) is labeled with both dyes. The fourth nucleotide (shown as G in FIG. 2C) is unlabeled.

There are a number of ways to attach and, when necessary, cleave the fluorescent labels. For example, the fluorescent labels may be attached to a base, in which case they may be cleaved chemically. As another example, the fluorescent labels may be attached to a phosphate, in which case they may be cleaved by polymerase or, if attached via a linker, by cleaving the linker.

In some embodiments, the fluorescent label is linked to the nitrogenous base (A, C, T, G, or a derivative) of the nucleotide precursor. After incorporation of the nucleotide precursor and the detection of the emitted light, the fluorescent label is cleaved from the incorporated nucleotide.

In some embodiments, the fluorescent label is attached via a cleavable linker. Cleavable linkers are known in the art and have been described, e.g., in U.S. Pat. Nos. 7,057,026, 7,414,116 and continuations and improvements thereof. In some embodiments, the fluorescent label is attached to the 5-position in pyrimidines or the 7-position in purines via a linker comprising an allyl or azido group. In other embodiments, the linker comprises a disulfide, indole, a Sieber group, a t-butyl Sieber group, or dialkoxybenzyl group. The linker may further contain one or more substituents selected from alkyl ($C_{1-6}$) or alkoxy ($C_{1-6}$), nitro, cyano, fluoro groups or groups with similar properties. Briefly, the linker can be cleaved by water-soluble phosphines or phosphine-based transition metal-containing catalysts. Other linkers and linker cleavage mechanisms are known in the art. For example, linkers comprising trityl groups, p-alkoxybenzyl ester groups, p-alkoxybenzyl amides groups, tert-butyloxycarbonyl (Boc) groups, and acetal based groups can be cleaved under acidic conditions by a proton-releasing cleavage agent, such as an acid. A thioacetal or other sulfur-containing linker can be cleaved using a thiophilic metals, such as nickel, silver or mercury. The cleavage protecting groups can also be considered for the preparation of suitable linker molecules. Ester- and disulfide containing linkers can be cleaved under reductive conditions. Linkers containing triisopropyl silane (TIPS) or t-butyldimethyl silane (TBDMS) can be cleaved in the presence of F ions. Photocleavable linkers cleaved by a wavelength that does not affect other components of the reaction mixture include linkers comprising o-nitrobenzyl groups. Linkers comprising benzyloxycarbonyl groups can be cleaved by Pd-based catalysts.

In some embodiments, the nucleotide precursor comprises a fluorescent label attached to a polyphosphate moiety as described in, e.g., U.S. Pat. Nos. 7,405,281 and 8,058,031. Briefly, the nucleotide precursor comprises a nucleoside moiety and a chain of 3 or more phosphate groups where one or more of the oxygen atoms are optionally substituted, e.g., with S. The label may be attached to the $\alpha$, ($\beta$, $\gamma$ or higher phosphate group (if present) directly or via a linker. In some embodiments, the fluorescent label is attached to a phosphate group via a non-covalent linker as described, e.g., in U.S. Pat. No. 8,252,910. In some embodiments, the linker is a hydrocarbon selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl; see, e.g., U.S. Pat. No. 8,367,813. The linker may also comprise a nucleic acid strand; see, e.g., U.S. Pat. No. 9,464,107.

In embodiments in which the fluorescent label is linked to a phosphate group, the nucleotide precursor is incorporated into the nascent chain by the nucleic acid polymerase, which also cleaves and releases the detectable fluorescent label. In some embodiments, the fluorescent label is removed by cleaving the linker, e.g., as described in U.S. Pat. No. 9,587,275.

In some embodiments, the nucleotide precursors are non-extendable "terminator" nucleotides, i.e., the nucleotides that have a 3'-end blocked from addition of the next nucleotide by a blocking "terminator" group. The blocking groups are reversible terminators that can be removed in order to continue the strand synthesis process as described herein. Attaching removable blocking groups to nucleotide precursors is known in the art. See, e.g., U.S. Pat. Nos. 7,541,444, 8,071,739 and continuations and improvements thereof. Briefly, the blocking group may comprise an allyl group that can be cleaved by reacting in aqueous solution with a metal-allyl complex in the presence of phosphine or nitrogen-phosphine ligands.

In the embodiment illustrated in FIG. 2C, Image 1 is taken with the temperature within a first temperature range, and Image 2 is taken with the temperature within a second, lower temperature range. If the emitted intensity is below the threshold in both images, it is determined that the incorporated nucleotide is guanine (G). If the emitted intensity is above the threshold in Image 2 but below the threshold in Image 1, it is determined that the incorporated nucleotide is cytosine (C). If the emitted intensity is above the threshold in both images, adenine (A) and thymine (T) can be distinguished by comparing the intensity of emitted light in the two images. In the example of FIG. 2C, if the detected intensity is approximately the same in the two images, it can be determined that the incorporated nucleotide is thymine (T), because the first dye emits light of a known intensity in both temperature ranges. It is to be understood that the intensity of emitted light might be approximately the same in Images 1 and 2 when (in the example) thymine has been incorporated. The intensity would be approximately the same, for example, if the dye IV of FIG. 1C is used to label thymine. Alternatively, the intensity associated with thymine could be different in Image 1 and Image 2. For example, if the dye II of FIG. 1C were used to label thymine, the measured intensity in the two images may be different. It would, however, be known what intensity to expect from the dye labeling thymine at the respective temperatures at which Images 1 and 2 are taken.

Because the third nucleotide (shown as adenine (A) in FIG. 2C) has been labeled with two dyes, one of which also labels thymine (T), and the intensity emitted by the dye labeling thymine is known for the two temperatures at which Images 1 and 2 are taken, it can be determined whether adenine (A) or thymine (T) has been incorporated because the emitted intensity of Image 2 will be higher when the incorporated nucleotide is adenine (A) than when it is thymine (T). Thus, if the detected intensity is higher in Image 2 than in Image 1, and it is greater than the expected emitted intensity for the dye labeling thymine (T), it can be determined that the incorporated nucleotide is adenine (A). One advantage of this embodiment is that there is no need to add any chemical reagents to change or remove any labels between taking the two images. The incorporated nucleotide can be determined simply by comparing the detected intensity levels in Images 1 and 2. The table below provides the decision table associated with the example shown in FIG. 2C and described above, where threshold 1 is the intensity threshold to detect the first dye in temperature Range 1; threshold 2, which may be the same as or different from threshold 1, is the intensity threshold to detect the first dye in temperature Range 2; threshold 3 is the intensity threshold to detect the second dye in temperature Range 2; and threshold 4, which is greater than both of thresholds 2 and 3, is the intensity threshold to detect the presence of both the first and second dyes in temperature Range 2.

| Image 1 intensity | Image 2 intensity | Determination |
|---|---|---|
| <threshold 1 | <threshold 2 | guanine (G) |
| <threshold 1 | ≥threshold 3 | cytosine (C) |
| ≥threshold 1 | ≥threshold 2 and <threshold 4 | thymine (T) |
| ≥threshold 1 | ≥threshold 4 | adenine (A) |

One benefit of the approach shown in FIG. 2C and described above is that it does not require any additional chemistry steps within a cycle, unlike conventional approaches using two imaging events.

Figure 3A:
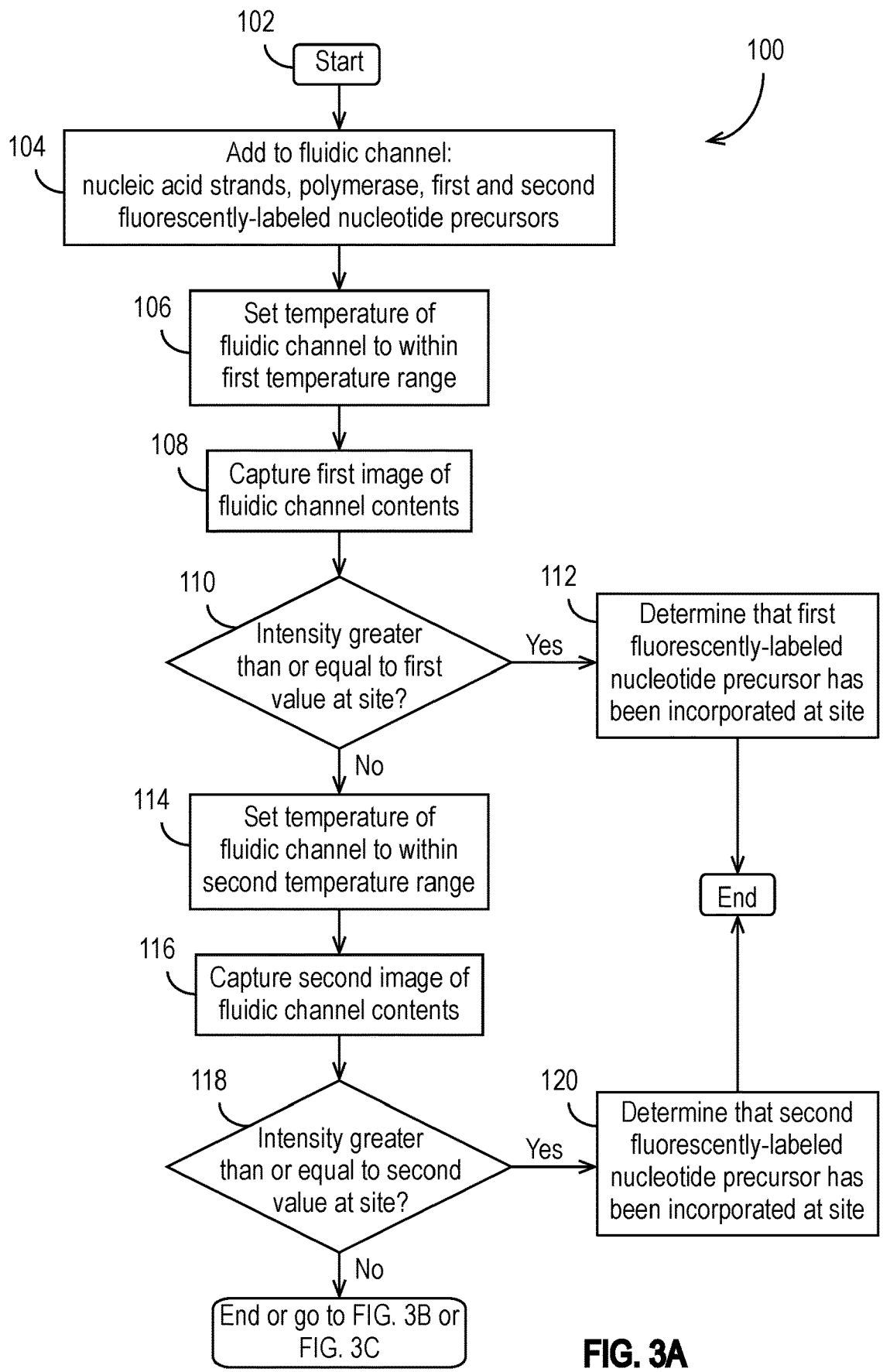
FIG. 3A is a flowchart illustrating a method of sequencing nucleic acid in accordance with some embodiments.

FIG. 3A is a flowchart illustrating a method 100 of sequencing nucleic acid in accordance with some embodiments. The method 100 involves the use of a sequencing apparatus comprising a fluidic channel having a plurality of sites for binding a plurality of molecules of a nucleic acid polymerase or a plurality of nucleic acid strands (e.g., as described above and as is known in the art) to a surface of the fluidic channel. At 102 the method begins. At 104, material is added to the fluidic channel. The material includes at least the plurality of nucleic acid strands, the plurality of molecules of the nucleic acid polymerase, a first fluorescently-labeled nucleotide precursor, and a second fluorescently-labeled nucleotide precursor.

The materials added in step 104 may be added to the fluidic channel at the same time or in one or more rounds of addition. For example, in some embodiments, molecules of a nucleic acid polymerase are first bound to the surface of the fluidic channel at the sites, and then the remaining materials are added to the fluidic channel. In other embodiments, nucleic acid strands are first bound to the surface of the fluidic channel at the sites, and then the remaining materials are added to the fluidic channel.

The first fluorescently-labeled nucleotide precursor comprises a first fluorescent label (which may be cleavable). The intensity emitted by the first fluorescent label is greater than or equal to a first threshold in a first temperature range and also in a second temperature range that is lower than and does not overlap the first temperature range. In other words, the first fluorescent label will emit light at an intensity of at least the first threshold in both the first and second temperature ranges. The first and second temperature ranges can be adjacent (e.g., the first temperature range is from 30 to 50 degrees Celsius and the second temperature range is from 10 to 30 degrees Celsius), or they can be separated by a gap in temperatures (e.g., the first temperature range is from 40 to 50 degrees Celsius, and the second temperature range is from 20 to 35 degrees Celsius).

The second fluorescently-labeled nucleotide precursor comprises a second fluorescent label (which may be cleavable). The intensity emitted by the second fluorescent label is less than a second threshold in the first temperature range and greater than or equal to the second threshold in the second temperature range. In other words, considering only the first and second temperature ranges, the second fluorescent label will emit light at an intensity of at least the second threshold only in the second (lower) temperature range; in the first (higher) temperature range, the second fluorescent label will not emit light at an intensity that meets or exceeds the second threshold. The first and second thresholds may be the same, or they may be different. It is to be appreciated that the second fluorescent label may emit light at an intensity of at least the second threshold in temperature ranges outside of the first and second temperature ranges. For example, the second fluorescent label may emit light at an intensity of at least the second threshold at temperatures below the second temperature range. It is also contemplated that the second fluorescent label may emit light at an intensity of at least the second threshold at temperatures above the first temperature range.

There are a number of ways to attach and, if necessary, cleave the fluorescent labels. For example, the fluorescent labels may be attached to a base, in which case they may be cleaved chemically. As another example, the fluorescent labels may be attached to a phosphate, in which case they may be cleaved by polymerase or, if attached via a linker, by cleaving the linker.

In some embodiments, the fluorescent label is linked to the nitrogenous base (A, C, T, G, or a derivative) of the nucleotide precursor. After incorporation of the nucleotide precursor and detection, the fluorescent label is cleaved from the incorporated nucleotide.

In some embodiments, the fluorescent label is attached via a cleavable linker. Cleavable linkers are known in the art and have been described, e.g., in U.S. Pat. Nos. 7,057,026, 7,414,116 and continuations and improvements thereof. In some embodiments, the fluorescent label is attached to the 5-position in pyrimidines or the 7-position in purines via a linker comprising an allyl or azido group. In other embodiments, the linker comprises a disulfide, indole, a Sieber group, a t-butyl Sieber group, or a dialkoxybenzyl group. The linker may further contain one or more substituents selected from alkyl ($C_{1-6}$) or alkoxy ($C_{1-6}$), nitro, cyano, fluoro groups or groups with similar properties. Briefly, the linker can be cleaved by water-soluble phosphines or phosphine-based transition metal-containing catalysts. Other linkers and linker cleavage mechanisms are known in the art.

For example, linkers comprising trityl groups, p-alkoxybenzyl ester groups, p-alkoxybenzyl amide groups, tert-butyloxycarbonyl (Boc) groups, and acetal based groups can be cleaved under acidic conditions by a proton-releasing cleavage agent, such as an acid. A thioacetal or other sulfur-containing linker can be cleaved using a thiophilic metals, such as nickel, silver or mercury. The cleavage protecting groups can also be considered for the preparation of suitable linker molecules. Ester- and disulfide containing linkers can be cleaved under reductive conditions. Linkers containing triisopropyl silane (TIPS) or t-butyldimethyl silane (TBDMS) can be cleaved in the presence of F ions. Photocleavable linkers cleaved by a wavelength that does not affect other components of the reaction mixture include linkers comprising o-nitrobenzyl groups. Linkers comprising benzyloxycarbonyl groups can be cleaved by Pd-based catalysts.

In some embodiments, the nucleotide precursor comprises a label attached to a polyphosphate moiety as described in, e.g., U.S. Pat. Nos. 7,405,281 and 8,058,031. Briefly, the nucleotide precursor comprises a nucleoside moiety and a chain of 3 or more phosphate groups where one or more of the oxygen atoms are optionally substituted, e.g., with S. The label may be attached to the α, (β, γ or higher phosphate group (if present) directly or via a linker. In some embodiments, the label is attached to a phosphate group via a non-covalent linker as described, e.g., in U.S. Pat. No. 8,252,910. In some embodiments, the linker is a hydrocarbon selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl; see, e.g., U.S. Pat. No. 8,367,813. The linker may also comprise a nucleic acid strand; see, e.g., U.S. Pat. No. 9,464,107.

In embodiments in which the fluorescent label is linked to a phosphate group, the nucleotide precursor is incorporated into the nascent chain by the nucleic acid polymerase, which also cleaves and releases the detectable fluorescent label. In some embodiments, the fluorescent label is removed by cleaving the linker, e.g., as described in U.S. Pat. No. 9,587,275.

In some embodiments, the nucleotide precursors are non-extendable "terminator" nucleotides, i.e., the nucleotides that have a 3'-end blocked from addition of the next nucleotide by a blocking "terminator" group. The blocking groups are reversible terminators that can be removed in order to continue the strand synthesis process as described herein. Attaching removable blocking groups to nucleotide precursors is known in the art. See, e.g., U.S. Pat. Nos. 7,541,444, 8,071,739 and continuations and improvements thereof. Briefly, the blocking group may comprise an allyl group that can be cleaved by reacting in aqueous solution with a metal-allyl complex in the presence of phosphine or nitrogen-phosphine ligands. Other examples of reversible terminator nucleotides used in sequencing by synthesis are known in the art.

Referring again to FIG. 3A, at 106, after the nucleic acid strands, polymerase molecules, and first and second fluorescently-labeled nucleotide precursors have been added to the fluidic channel, the temperature of the contents of the fluidic channel is set to be within the first temperature range. At 108, the apparatus is illuminated (e.g., by a laser) while the temperature is within the first temperature range, and a first image of the contents of the fluidic channel is captured, i.e., a first intensity at each of the plurality of sites is detected while the temperature of the fluidic channel is within the first temperature range. The first image captures the intensity at each of the plurality of sites. As explained previously, an image is a record of the presence or absence of emitted light (e.g., an optical response over a plurality of physical locations).

At 110, the image is assessed to determine whether the intensity of the first image at a particular site of the plurality of sites is greater than or equal to a first value. If the intensity of the first image at the particular site is greater than or equal to the first value, then, at 112 it is determined that the first fluorescently-labeled nucleotide precursor has been incorporated into the extendable primer at that site. The same approach can be used to determine, for some or all of the other sites, whether the first fluorescently-labeled nucleotide precursor has been incorporated into the extendable primer at those sites.

If, at 110, it is determined that the intensity of the first image at the particular site is not greater than or equal to the first value, at 114 the temperature of the fluidic channel's contents is set to be within the second (lower) temperature range. At 116, the apparatus is illuminated (e.g., by a laser) while the temperature is within the second temperature range, and a second image of the contents of the fluidic channel is captured, i.e., a second intensity at each of the plurality of sites is detected while the temperature of the fluidic channel is within the second temperature range. The second image captures the intensity at each of the plurality of sites. At 118, it is determined whether the intensity of the second image at a particular site of the plurality of sites is greater than or equal to a second value and whether the intensity of the first image at the particular site is less than the first value. The first and second values may be approximately the same, or they may be different. In some embodiments, the first value is the first threshold, and the second value is the second threshold. In some embodiments, the first value is based on the first threshold, and the second value is based on the second threshold. For example, the first value may be a multiple of the first threshold or a percentage of the first threshold. Similarly, the second value may be multiple of the second threshold or a percentage of the second threshold.

If the intensity of the second image at a particular site of the plurality of sites is greater than or equal to a second value and the intensity of the first image at the particular site is less than the first value, then at 120 it is determined that the second fluorescently-labeled nucleotide precursor has been incorporated into the extendable primer at that site. The same approach can be used to determine, for some or all of the other sites, whether the second fluorescently-labeled nucleotide precursor has been incorporated into the extendable primer at those sites.

As explained above, the method 100 illustrated in FIG. 3A enables a determination of whether either of the two fluorescently-labeled nucleotide precursors has been incorporated during a cycle of a nucleotide sequencing process. The steps 104 through 120 can be performed again in one or more subsequent sequencing cycles, e.g., after cleaving the first and second fluorescent labels.

As described in more detail below, in some embodiments, the method 100 includes steps beyond those shown in FIG. 3A. For example, in some embodiments, the method 100 includes steps illustrated in FIG. 3B or the steps illustrated in FIG. 3C.

Figure 3B:
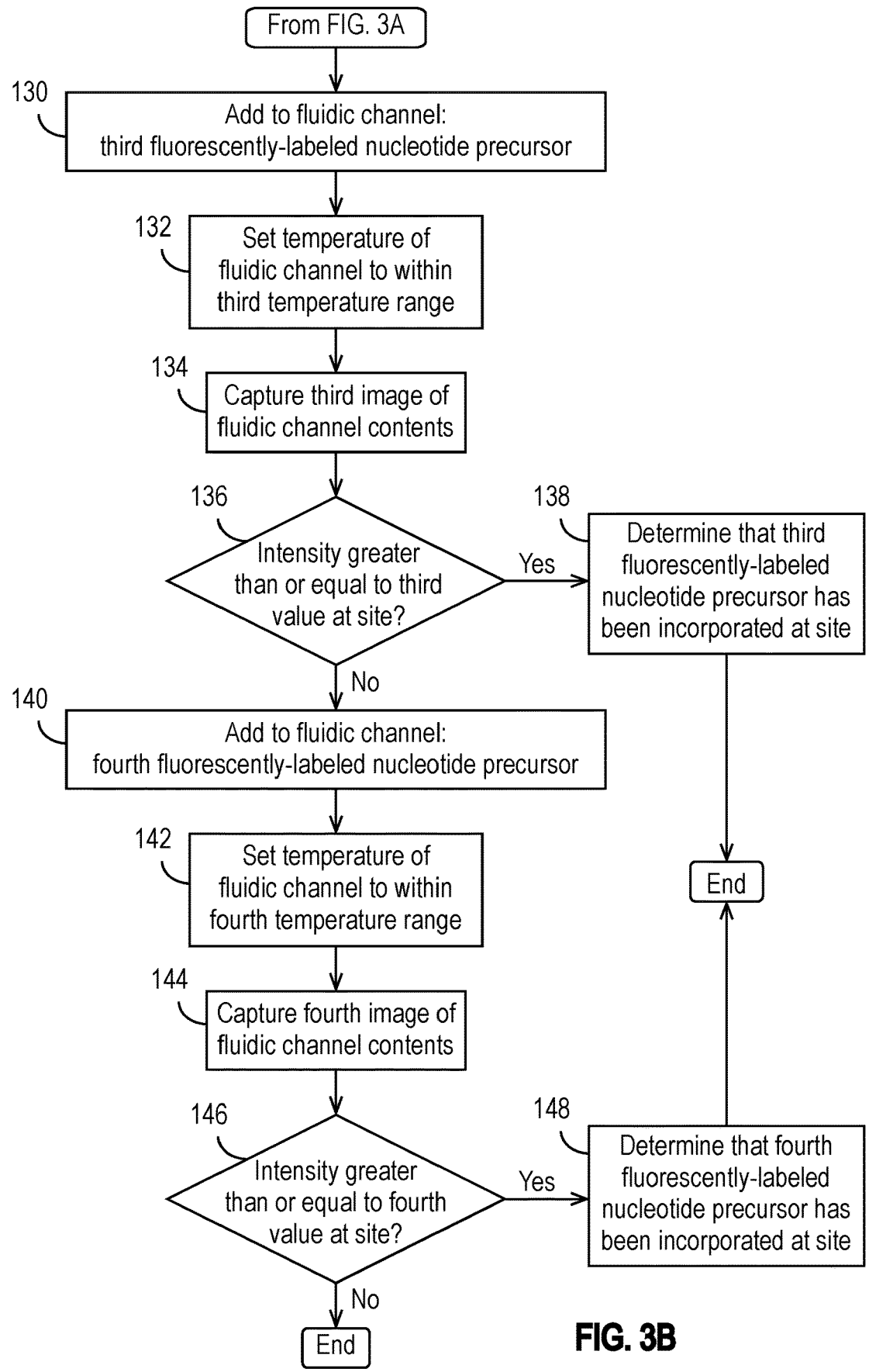
FIG. 3B illustrates how the method can continue after FIG. 3A in accordance with some embodiments.
Figure 3C:
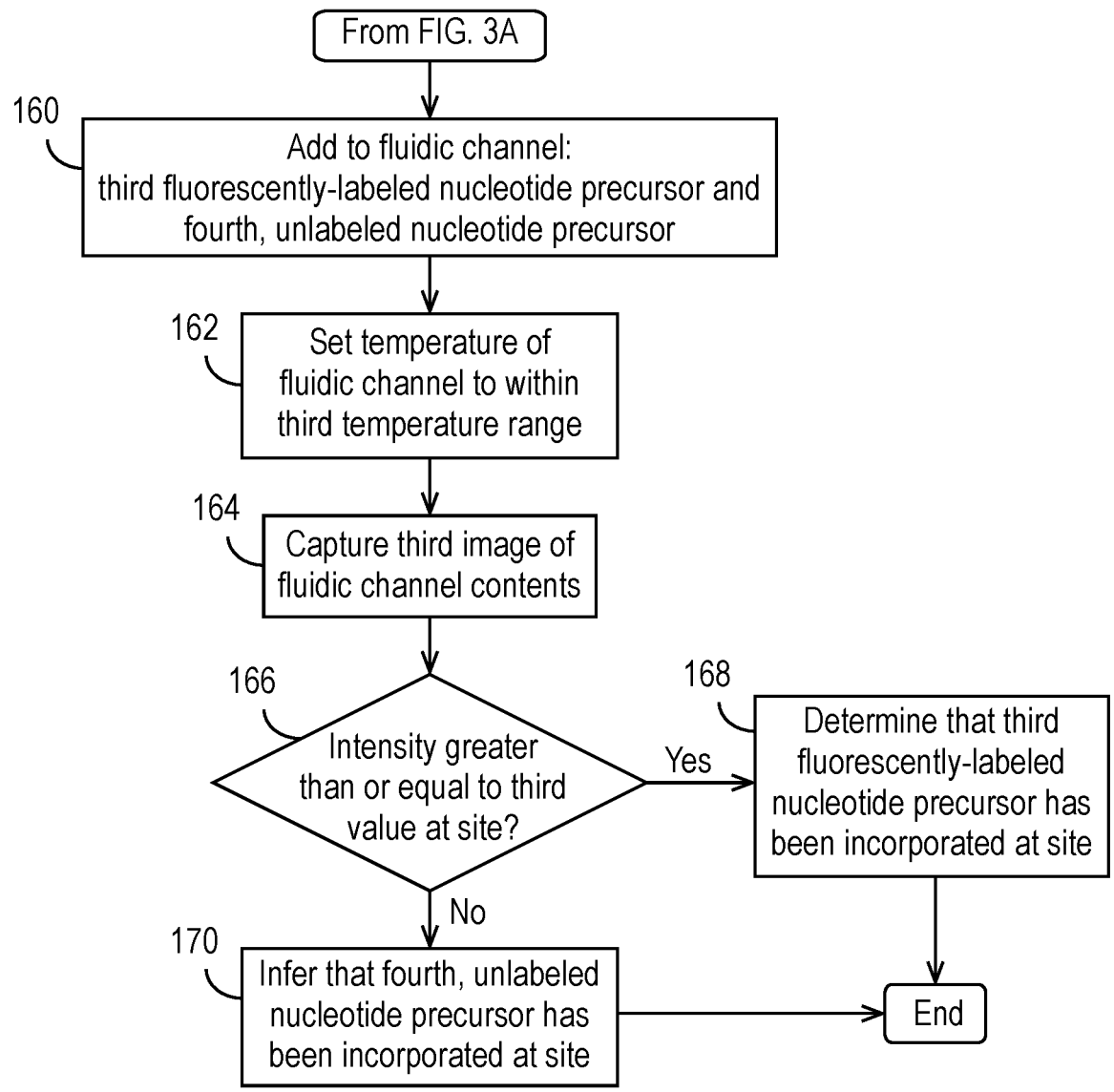
FIG. 3C illustrates another way the method can continue after FIG. 3A in accordance with some embodiments.
Figure 3D:
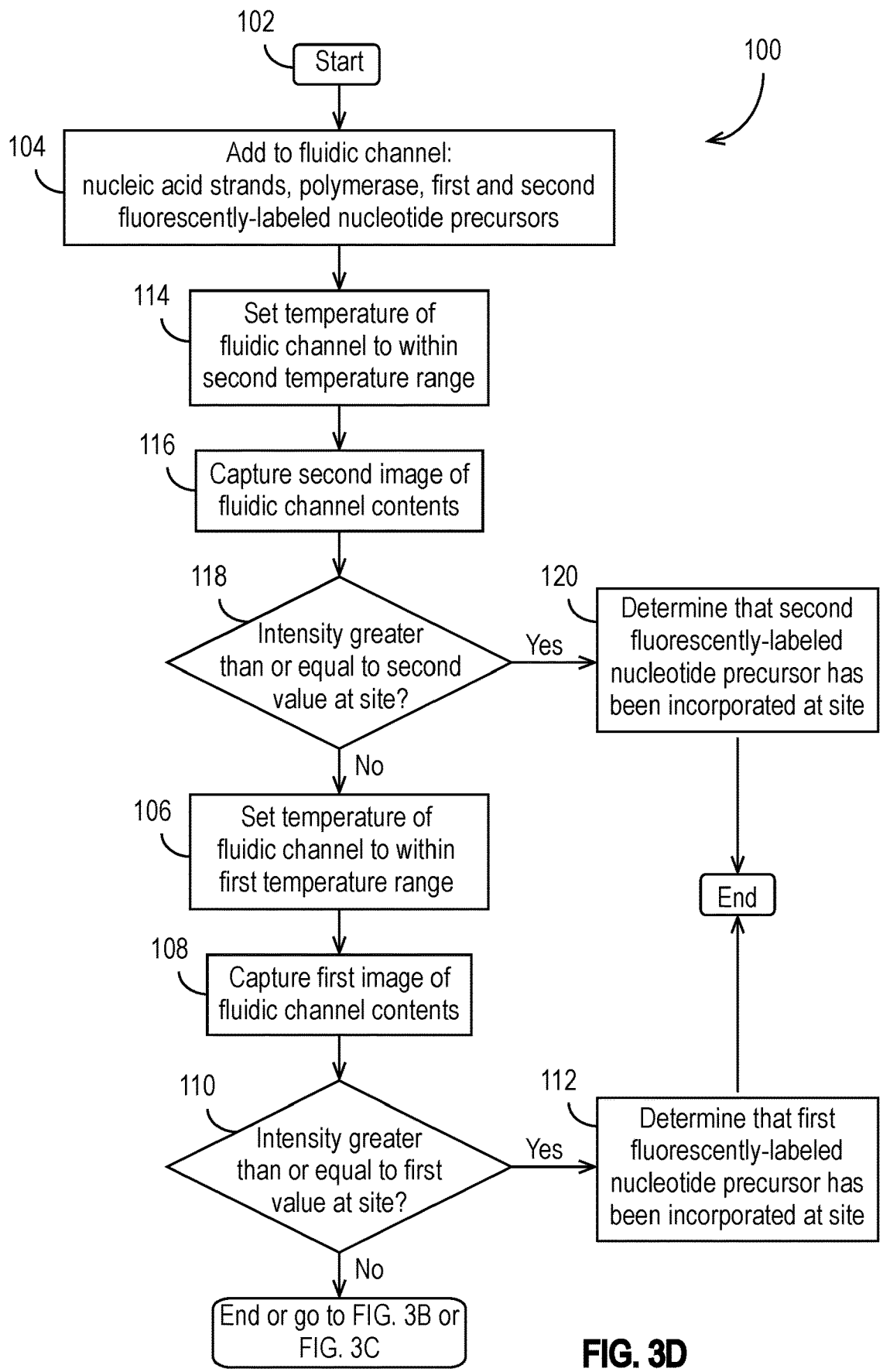
FIG. 3D illustrates an alternative ordering of elements of the method illustrated in FIG. 3A in accordance with some embodiments.

It is to be appreciated that although FIG. 3A illustrates the method 100 as if the temperature of the contents of the fluidic channel is initially set to be within the highest temperature range and then cooled, an implementation could begin with the temperature in the second temperature range and then heat the contents of the fluidic chamber to be within the first (higher) temperature range. Such an embodiment is shown in FIG. 3D. As shown, the steps associated with the first temperature range and the first image may take place after the steps associated with the second temperature range and the second image.

Figure 3E:
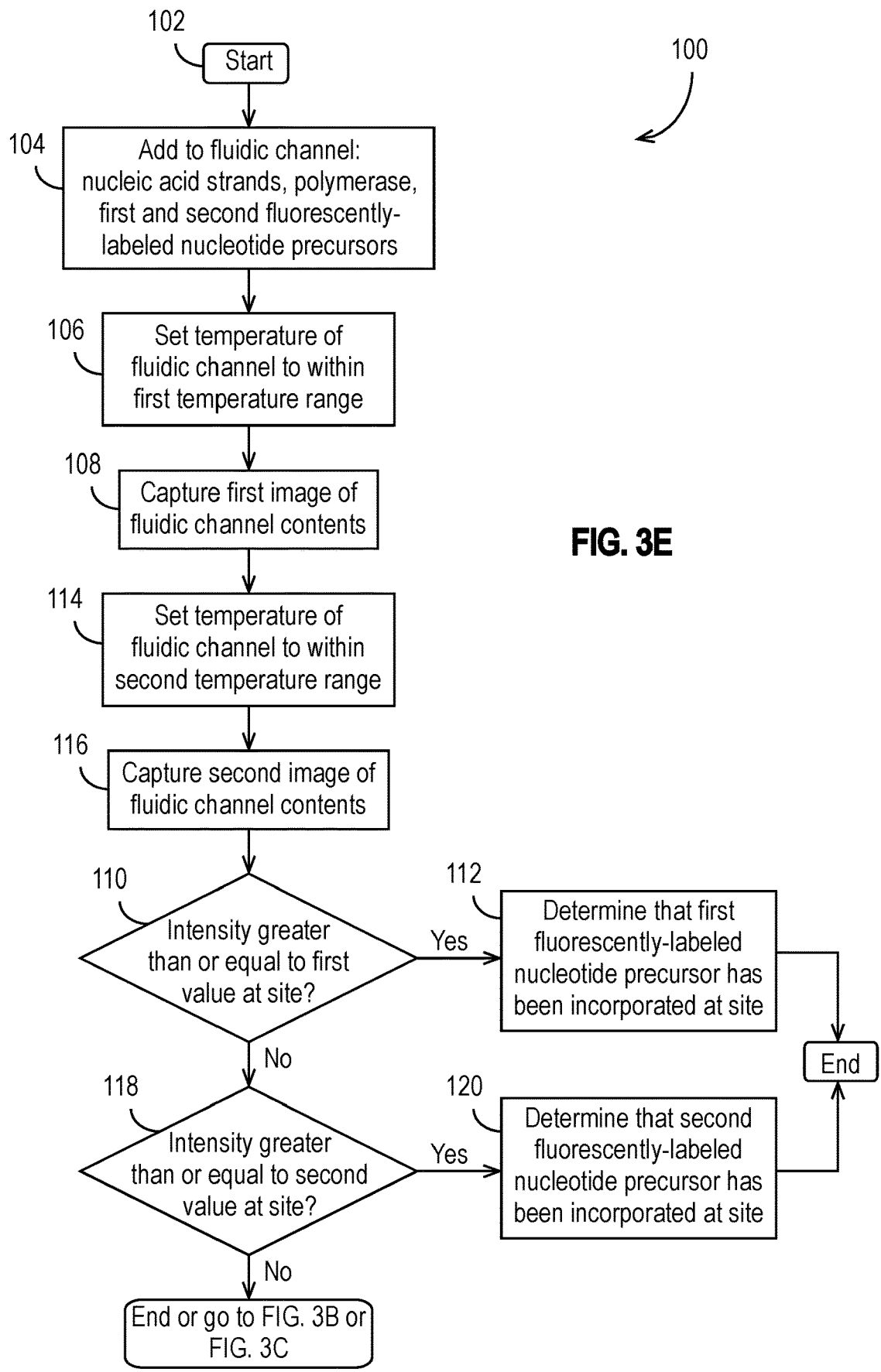
FIG. 3E illustrates another alternative ordering of elements of the method illustrated in FIG. 3A in accordance with some embodiments.

Referring again to FIG. 3A, in some embodiments the method 100 terminates after 112 because it has been determined that the first fluorescently-labeled nucleotide precursor has been incorporated at the site. It is to be appreciated, however, that although FIG. 3A shows the steps occurring in a particular order (e.g., step 110 occurring before step 114), various of the steps can occur in a different order than shown. For example, as explained above in the context of FIG. 3D, the lower temperature range may be tested first. As another example, it is not necessary to make the determination of whether the intensity is greater than or equal to a specified value between imaging steps. In some embodiments, the first and second images are captured, and then the images are analyzed to determine whether the first or second fluorescently-labeled nucleotide precursor was incorporated. FIG. 3E illustrates such an embodiment. It is to be understood that although FIG. 3E illustrates steps 106 and 108 taking place before steps 114 and 116, steps 114 and 116 may be performed before steps 106 and 108.

Referring again to FIG. 3A, if, at 118, it is determined that the intensity of the second image at the particular site is not greater than or equal to the second value or the intensity of the first image at the particular site is not less than the first value, then it is concluded that neither the first nor the second fluorescently-labeled nucleotide precursor has been incorporated at the particular site. In that case, the method 100 can end, or further analysis can be performed. FIG. 3B illustrates how the method 100 can continue in accordance with some embodiments. FIG. 3B shows the steps to determine whether at least a third fluorescently-labeled nucleotide precursor has been incorporated at the particular site. FIG. 3B also provides for the determination of whether a fourth fluorescently-labeled nucleotide precursor has been incorporated at the particular site. The combination of FIG. 3A and FIG. 3B shows a method 100 of implementing the approach illustrated in FIG. 2A, discussed above.

Referring to FIG. 3B, at 130, a third fluorescently-labeled nucleotide precursor is added to the fluidic channel. Step 130 may be combined with step 104 shown FIG. 3A (i.e., the first, second, and third fluorescently-labeled nucleotide precursors may be added to the fluid chamber at substantially the same time), or it may be a separate step. The third fluorescently-labeled nucleotide precursor comprises a third fluorescent label (which may be cleavable). The intensity emitted by the third fluorescent label is less than a third threshold in the first and second temperature ranges and greater than or equal to the third threshold in a third temperature range that is lower than both the first and second temperature ranges. In other words, considering only the first, second, and third temperature ranges, the third fluorescent label will emit light at an intensity of at least the third threshold only in the third temperature range; in the higher first and second temperature ranges, the third fluorescent label will not emit light at an intensity that meets or exceeds the third threshold. The first, second, and third temperature ranges are non-overlapping, and they may be adjacent to each other, or there may be a temperature gap between the first and second temperature ranges and/or between the second and third temperature ranges. It is to be appreciated that the third fluorescent label may emit light at an intensity of at least the third threshold in temperature ranges outside of the first, second, and third temperature ranges. For example, the third fluorescent label may emit light at an intensity of at least the third threshold at temperatures below the third temperature range. It is also contemplated that the third fluorescent label may emit light at an intensity of at least the third threshold at temperatures above the first temperature range. The third threshold may be approximately the same as (i.e., equal to) the first threshold and/or the second threshold. Alternatively, the third threshold may be different from the first threshold and/or the second threshold.

At 132, the temperature of the contents of the fluidic channel is set to be within the third temperature range. At 134, the apparatus is illuminated while the temperature is within the third temperature range, and a third image of the contents of the fluidic channel is captured, i.e., a third intensity at each of the plurality of sites is detected while the temperature of the fluidic channel is within the third temperature range. The third image captures the intensity at each of the plurality of sites.

At 136, the third image is assessed to determine whether the intensity of the third image at a particular site of the plurality of sites is greater than or equal to a third value. The third value may be approximately the same as (or equal to) the first value and/or the second value. If the intensity of the third image at the particular site is greater than or equal to the third value, and the intensity of the first image at the particular site is less than the first value, and the intensity of the second image at the particular site is less than the second value, then, at 138, it is determined that the third fluorescently-labeled nucleotide precursor has been incorporated into the extendable primer at that site. The same approach can be used to determine, for some or all of the other sites, whether the third fluorescently-labeled nucleotide precursor has been incorporated into the extendable primer at those sites.

If, at 136, it is determined that the intensity of the third image at the particular site is not greater than or equal to the third value, at 140, a fourth fluorescently-labeled nucleotide precursor is added to the fluidic chamber. Step 140 may be combined with step 130 and/or step 104 (shown in FIG. 3A). The fourth fluorescently-labeled nucleotide precursor comprises a fourth fluorescent label (which may be cleavable). The intensity emitted by the fourth fluorescent label is less than a fourth threshold in the first, second, and third temperature ranges and greater than or equal to the fourth threshold in a fourth temperature range that is lower than all of the first, second, and third temperature ranges. In other words, considering only the first, second, third, and fourth temperature ranges, the fourth fluorescent label will emit light at an intensity of at least the fourth threshold only in the fourth temperature range; in the higher first, second, and third temperature ranges, the fourth fluorescent label will not emit light at an intensity that meets or exceeds the fourth threshold. It is to be appreciated that the fourth fluorescent label may emit light at an intensity of at least the fourth threshold in temperature ranges outside of the first, second, third, and fourth temperature ranges. For example, the fourth fluorescent label may emit light at an intensity of at least the fourth threshold at temperatures below the fourth temperature range. It is also contemplated that the fourth fluorescent label may emit light at an intensity of at least the fourth threshold at temperatures above the first temperature range. The first, second, third, and fourth temperature ranges are non-overlapping, and they may be adjacent to each other, or there may be a temperature gap between the first and second temperature ranges, between the second and third temperature ranges, and/or between the third and fourth temperature ranges. The fourth threshold may be approximately the same as (i.e., equal to) the first threshold, the second threshold, and/or the third threshold, or it may be different from the first, second, and/or third thresholds.

At 142, the temperature of the fluidic channel's contents is set to be within the fourth temperature range. At 144, the apparatus is illuminated while the temperature is within the fourth temperature range, and a fourth image of the contents of the fluidic channel is captured, i.e., a fourth intensity at each of the plurality of sites is detected while the temperature of the fluidic channel is within the fourth temperature range. The fourth image captures the intensity at each of the plurality of sites. At 146, it is determined whether the intensity of the fourth image at a particular site of the plurality of sites is greater than or equal to a fourth value. The fourth value may be approximately the same as (i.e., equal to) the first value, the second value, and/or third value. If so, and if the intensity of the first image at the particular site is less than the first value, and the intensity of the second image at the particular site is less than the second value, and the intensity of the third image at the particular site is less than the third value, then, at 148 it is determined that the fourth fluorescently-labeled nucleotide precursor has been incorporated into the extendable primer at that site. The same approach can be used to determine, for some or all of the other sites, whether the fourth fluorescently-labeled nucleotide precursor has been incorporated into the extendable primer at those sites.

It is to be understood that FIG. 3D or FIG. 3E can be substituted for FIG. 3A. Likewise, it is to be understood that changes similar to those described above in the context of FIGS. 3D and 3E can be made to the combination of FIG. 3A and FIG. 3B. Specifically, the order in which the temperature ranges are tested need not be from highest to lowest, or even monotonic (i.e., it is contemplated that the temperature ranges may be tested in any order). Similarly, it is not necessary to analyze each image after it is taken and before changing the temperature of the contents of the fluidic channel (i.e., two or more images may be taken prior to any analysis). In addition, and as explained above, when more than two nucleotide precursors are to be added to the fluidic chamber, they may be added in one or more rounds of addition (e.g., all materials can be added in step 104, or two or more of steps 104, 130, and 140 can be combined).

As explained above in the context of FIG. 2B, some embodiments use only three images to enable determination of which of four nucleotide precursors has been incorporated at a particular site. The combination of FIGS. 3A and 3C illustrates the method 100 in accordance with some such embodiments. After step 118 (FIG. 3A), the method 100 continues with step 160, in which a third fluorescently-labeled nucleotide precursor and a fourth, unlabeled nucleotide precursor are added to the fluidic channel. Step 160 may be combined with step 104 (FIG. 3A), or it may be a separate step. The third fluorescently-labeled nucleotide precursor comprises the third fluorescent label, as described above. The fourth nucleotide precursor is unlabeled.

At 162, the temperature of the contents of the fluidic channel is set to be within the third temperature range. At 164, the apparatus is illuminated while the temperature is within the third temperature range, and a third image of the contents of the fluidic channel is captured, i.e., a third intensity at each of the plurality of sites is detected while the temperature of the fluidic channel is within the third temperature range. The third image captures the intensity at each of the plurality of sites.

At 166, the third image is assessed to determine whether the intensity of the third image at a particular site of the plurality of sites is greater than or equal to a third value. The third value may be approximately the same as (i.e., equal to) the first value and/or the second value, or it may be different. If the intensity of the third image at the particular site is greater than or equal to the third value, and the intensity of the first image at the particular site is less than the first value, and the intensity of the second image at the particular site is less than the second value, then, at 168, it is determined that the third fluorescently-labeled nucleotide precursor has been incorporated into the extendable primer at that site. The same approach can be used to determine, for some or all of the other sites, whether the third fluorescently-labeled nucleotide precursor has been incorporated into the extendable primer at those sites.

If, at 166, it is determined that the intensity of the third image at the particular site is not greater than or equal to the third value, at 170, it is inferred that the fourth, unlabeled nucleotide precursor has been incorporated at the particular site.

Figure 4A:
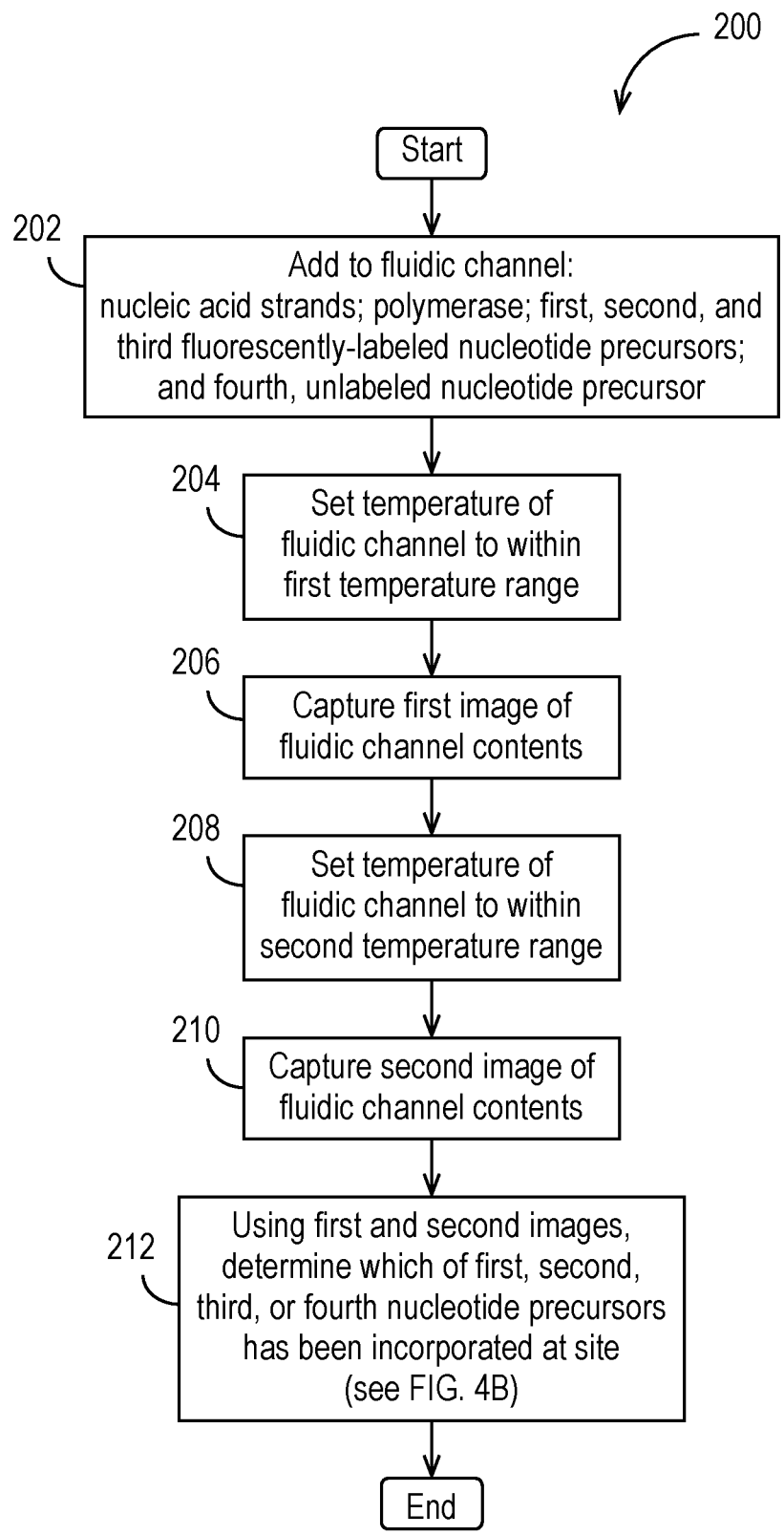
FIGS. 4A and 4B illustrate a method of sequencing nucleic acid in accordance with some embodiments.
Figure 4B:
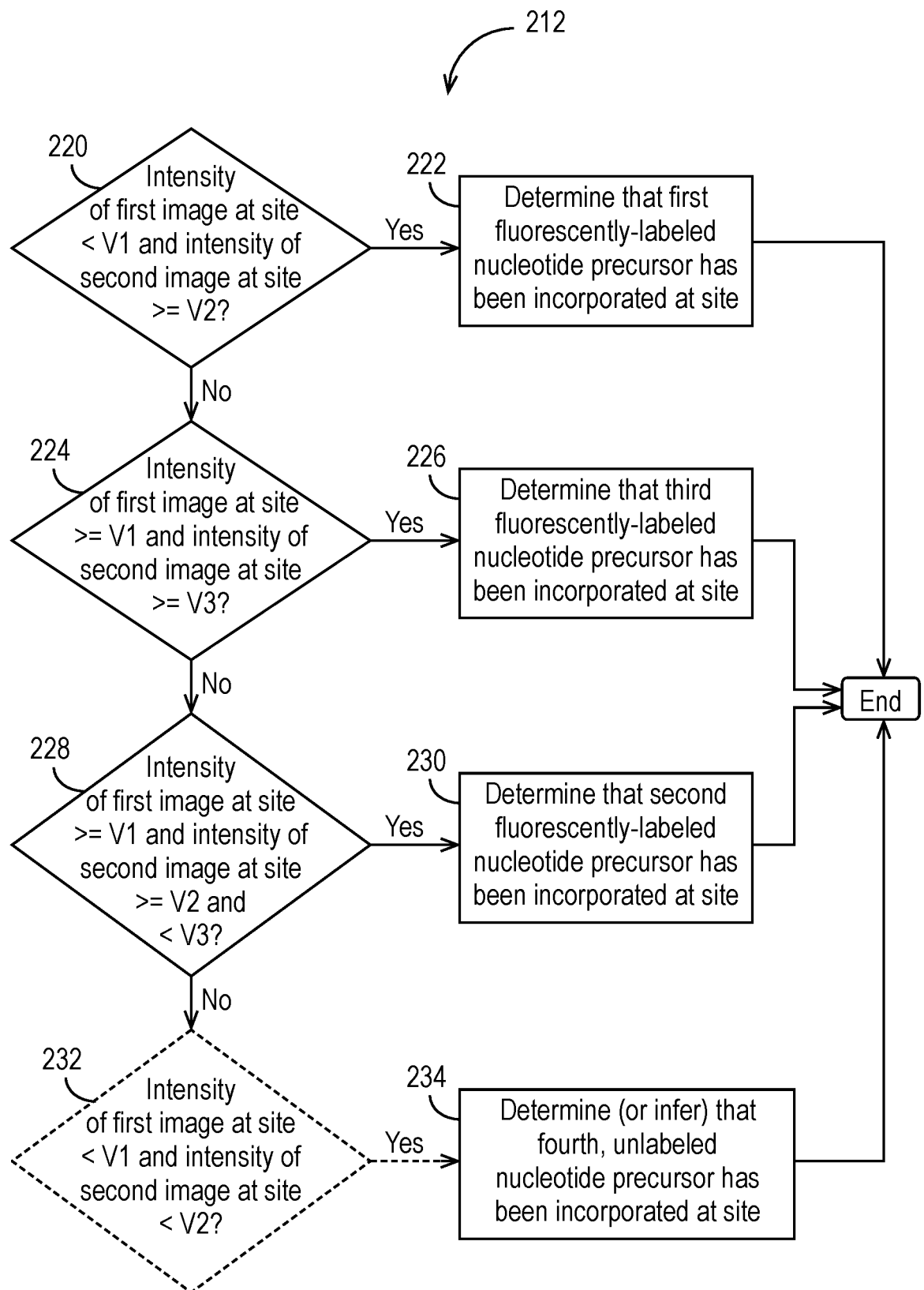

As explained above in the context of FIG. 2C, some embodiments use only two images to enable determination of which of four nucleotide precursors has been incorporated at a particular site. FIGS. 4A and 4B illustrate a method 200 in accordance with some such embodiments.

At 202, in one or more rounds of addition, material is added to the fluidic channel of a sequencing apparatus. The material includes at least a plurality of nucleic acid strands, a plurality of molecules of nucleic acid polymerase, a first fluorescently-labeled nucleotide precursor, a second fluorescently-labeled nucleotide precursor, a third fluorescently-labeled nucleotide precursor, and a fourth, unlabeled nucleotide precursor. The nucleic acid strands and nucleic acid polymerase were previously described in the context of FIG. 3A, and those descriptions are also applicable here. In addition, it was previously explained how the molecules of the nucleic acid polymerase or the plurality of nucleic acid strands can be bound to a surface of the fluidic channel of the sequencing apparatus. Those explanations apply here, too.

The first fluorescently-labeled nucleotide precursor comprises a first fluorescent label. The intensity emitted by the first fluorescent label is less than a first threshold in a first temperature range and greater than or equal to the first threshold in a second temperature range that is lower than the first temperature range. In other words, the first fluorescent label will emit light at an intensity of at least the first threshold in the second temperature range, but not in the first temperature range. The label need not be cleavable. It is to be appreciated that the first fluorescent label may emit light at an intensity of at least the first threshold in temperature ranges outside of the first and second temperature ranges. For example, the first fluorescent label may emit light at an intensity of at least the first threshold at temperatures below the second temperature range. It is also contemplated that the first fluorescent label may emit light at an intensity of at least the first threshold at temperatures above the first temperature range.

The second fluorescently-labeled nucleotide precursor comprises a second fluorescent label (which need not be cleavable). The intensity emitted by the second fluorescent label is greater than or equal to a second threshold in the first temperature range and in the second temperature range. In other words, considering only the first and second temperature ranges, the second fluorescent label will emit light at an intensity of at least the second threshold in both the first and second temperature ranges. The second threshold may be approximately the same as (i.e., equal to) the first threshold, or the two thresholds may be different.

The third fluorescently-labeled nucleotide precursor comprises both the first and second fluorescent labels.

The fourth nucleotide precursor does not include a fluorescent label.

There are a number of ways to attach the fluorescent labels to the first and second fluorescently-labeled nucleotide precursors, as described above in the context of FIG. 3A.

Referring again to FIG. 4A, at 204, the temperature of the contents of the fluidic channel is set to be within the first temperature range. At 206, the apparatus is illuminated while the temperature is within the first temperature range, and a first image of the contents of the fluidic channel is captured, i.e., a first intensity at each of the plurality of sites is detected while the temperature of the fluidic channel is within the first temperature range. The first image captures the intensity at each of the plurality of sites. At 208, the temperature of the contents of the fluidic channel is set to be within the second temperature range. At 210, the apparatus is illuminated while the temperature is within the second temperature range, and a second image of the contents of the fluidic channel is captured, i.e., a second intensity at each of the plurality of sites is detected while the temperature of the fluidic channel is within the second temperature range. The second image captures the intensity at each of the plurality of sites.

At 212, it is determined, using the first and second images, which of the first, second, third, or fourth nucleotide precursors has been incorporated at a particular site of the plurality of sites. FIG. 4B illustrates the step 212 in accordance with some embodiments. At 220, it is determined whether the intensity of the first image at the particular site is less than a first value and the intensity of the second image at the particular site is greater than or equal to a second value. The first and second values may be approximately the same (i.e., equal), or they may be different. The first and second values may be, respectively, equal to the first and second thresholds. Alternatively, the first and second values may be, respectively, based on the first and second thresholds (e.g., they may be multiples of or percentages of the first and second thresholds). If the intensity of the first image at the particular site is less than the first value and the intensity of the second image at the particular site is greater than or equal to the second value, then at 222 it is determined that the first fluorescently-labeled nucleotide precursor has been incorporated at the particular site. If not, then at 224 it is determined whether the intensity of the first image at the particular site is greater than or equal to the first value and the intensity of the second image at the particular site is greater than or equal to a third value, which is greater than each of the first and second values. The third value may be, for example, the sum of the first and second values. If the intensity of the first image at the particular site is greater than or equal to the first value and the intensity of the second image at the particular site is greater than or equal to the third value, then at 226 it is determined that the third fluorescently-labeled nucleotide precursor has been incorporated at the particular site. If not, then at 228 it is determined whether the intensity of the first image at the particular site is greater than or equal to the first value, and the intensity of the second image at the particular site is greater than or equal to the second value but less than the third value. If so, then at 230, it is determined that the second fluorescently-labeled nucleotide precursor has been incorporated at the particular site.

If it is not determined, at 228, that the intensity of the first image at the particular site is greater than or equal to the first value, and the intensity of the second image at the particular site is greater than or equal to the second value but less than the third value, then it can be inferred, at 234, that the fourth, unlabeled nucleotide precursor has been incorporated at the particular site. Alternatively, and optionally, it can be positively determined, at step 232, whether the intensity of the first image at the particular site is less than the first value, and the intensity of the second image at the particular site is less than the second value, in which case it is then determined, at 234, that the fourth, unlabeled nucleotide precursor has been incorporated at the particular site.

The explanations of FIGS. 3A-3E and FIGS. 4A and 4B presume that the emitted intensities of the fluorescent labels have characteristics and intensity profiles similar to those generally illustrated elsewhere in this document (e.g., in FIGS. 1A-1C and FIGS. 2A-2C). It is to be appreciated that it may be appropriate to modify certain of the elements of FIGS. 3A-3E (e.g., 110, 118, 136, 146, 166) and/or FIGS. 4A and 4B (e.g., 220, 224, 228, 232) if the intensities of the fluorescent labels have different characteristics (e.g., if they are non-monotonic with temperature). Those having ordinary skill in the art will understand, in view of the disclosures herein, what modifications are appropriate to make.

Figure 5:
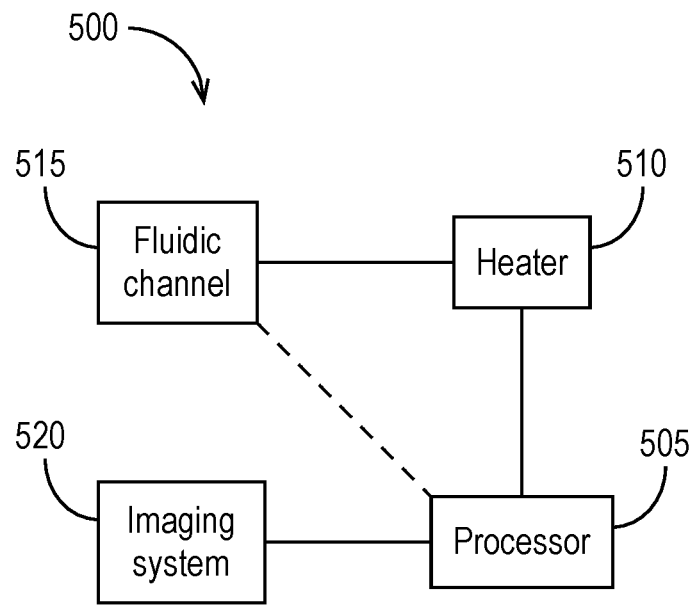
FIG. 5 is a block diagram of a system for sequencing nucleic acid in accordance with some embodiments.

FIG. 5 illustrates a system 500 for sequencing nucleic acid. The system 500 includes, as described previously, a fluidic channel 515 that has a plurality of sites for attaching, to a surface of the fluidic channel 515, a plurality of nucleic acid strands to be sequenced. For example, the fluidic channel 515 may include a structure (e.g., a cavity or a ridge) configured to anchor nucleic acid or a nucleic acid polymerase to the proximal wall. A heater 510 is coupled to the fluidic channel 515. The heater 510 sets the temperature of the contents of the fluidic channel 515. It is to be understood that the heater 510 may include cooling elements as well as or instead of heating elements. The primary characteristic of the heater 510 is that it is capable of controlling the temperature of the contents of the fluidic channel 515. For example, the heater 510 is capable of setting the temperature of the contents of the fluidic channel 515 to be within at least any of nonoverlapping first, second, third, and fourth temperature ranges. The second temperature range may be lower than the first temperature range, the third temperature range may be lower than the second temperature range, and the fourth temperature range may be lower than the third temperature range. The heater 510 may include, for example, thermal sensors, a microprocessor, or software.

The system 500 also includes an imaging system 520. The imaging system 520 is configured to detect the intensity at each of the plurality of sites of the fluidic channel 515. For example, the imaging system 520 is able to detect the intensity at each of the plurality of sites in each of the first, second, third, and fourth temperature ranges.

Figure 6:
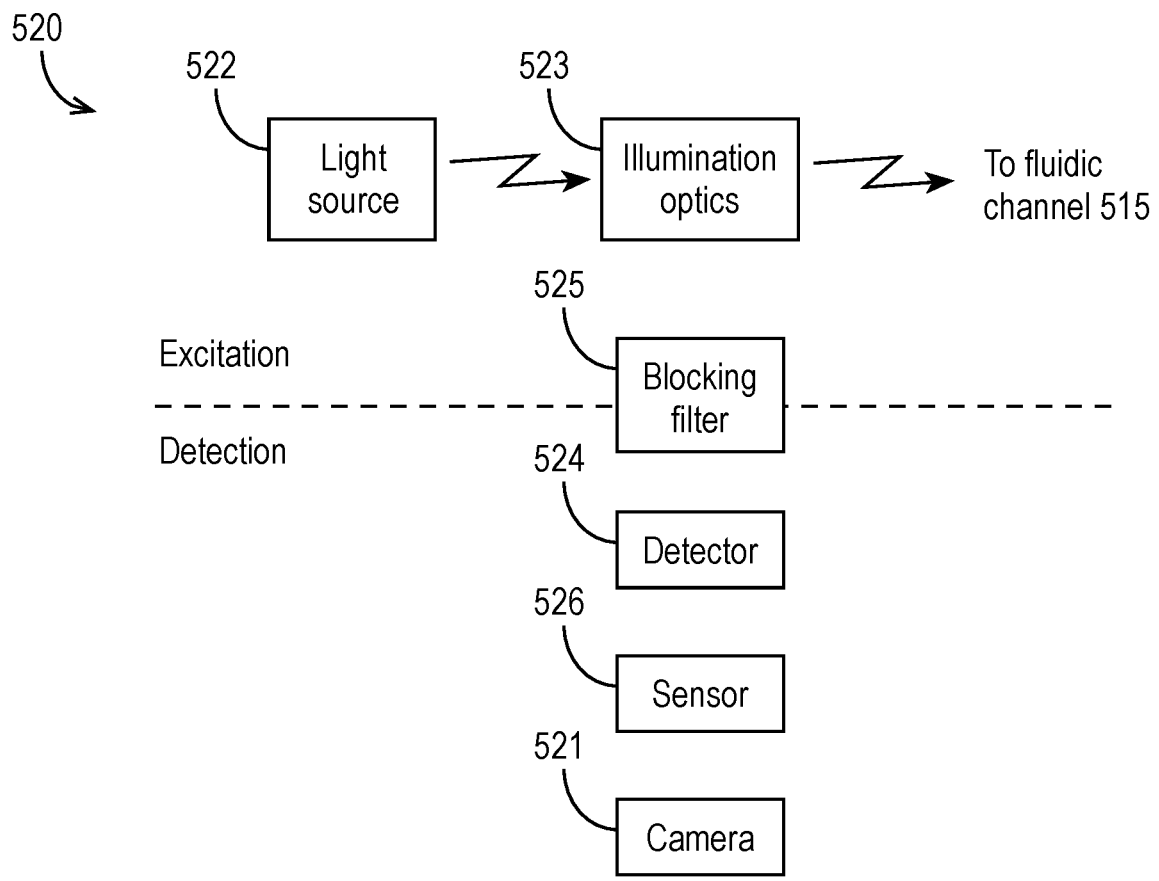
FIG. 6 is a block diagram of components of an imaging system that may be used in accordance with some embodiments.

As illustrated in FIG. 6, the imaging system 520 may comprise, for example, some or all of: a camera 521, an excitation light source 522 (e.g., a laser), illumination optics 523 (e.g., configured to uniformly distribute the excitation light and reduce stray light), a detector 524 (e.g., a lens having a large aperture to increase light collecting efficiency), an optical blocking filter 525 (e.g., to isolate the detector 524 from the excitation light), an analog-to-digital converter (ADC), and/or one or more sensors 526 to translate the detected intensity into a digitized signal or value (e.g., charge-coupled device (CCD) sensors, which may themselves include other components, such as ADCs). It is to be understood that the components and elements listed above are merely examples and are not intended to be limiting. The imaging system 520 may be coupled to a storage device (not shown). In such embodiments, the storage device may store intensity data collected by the imaging system 520.

The system 500 also includes at least one processor 505 coupled to the imaging system 520 and to the heater 510. The processor 505 executes machine-readable instructions. The processor 505 may direct or control other elements of the system 500. For example, the processor 505 may direct the heater 510 to set the temperature of the contents of the fluidic channel 515 to be within a specified range. Similarly, the processor 505 may direct the imaging system 520 to detect the intensity at all or a subset of the plurality of sites of the fluidic channel 515. In addition or alternatively, the processor 505 may obtain an indication of the detected intensity at all or a subset of the plurality of sites of the fluidic channel 515 from the imaging system.

For example, in response to the intensity at a particular site of the plurality of sites being greater than or equal to a first threshold in the first temperature range and in the second temperature range, the processor 505 may identify a first fluorescently-labeled nucleotide precursor or a complementary base of the first fluorescently-labeled nucleotide precursor. For example, if the processor 505 determines that the intensity at the particular site corresponds to the fluorescent label attached to a guanine precursor, the processor 505 may identify guanine as the detected label, or cytosine as the next base in the fragment of nucleic acid being sequenced.

Similarly, in response to the intensity at the particular site of the plurality of sites being less than a second threshold in the first temperature range and greater than or equal to the second threshold in the second temperature range, the processor 505 may identify a second fluorescently-labeled nucleotide precursor or a complementary base of the second fluorescently-labeled nucleotide precursor. Likewise, in response to the intensity at the particular site of the plurality of sites being less than a third threshold in the first and second temperature ranges and greater than or equal to the third threshold in the third temperature range, the processor 505 may identify a third fluorescently-labeled nucleotide precursor or a complementary base of the third fluorescently-labeled nucleotide precursor. And, finally, in response to the intensity at the particular site of the plurality of sites being less than a fourth threshold in each of the first, second, and third temperature ranges and greater than or equal to a fourth threshold in the fourth temperature range, the processor 505 may identify a fourth fluorescently-labeled nucleotide precursor or a complementary base of the fourth fluorescently-labeled nucleotide precursor.

The processor 505 may instruct the heater 510 to set the temperature of the contents within the fluidic channel to be within the first temperature range. The processor 505 may then obtain, from the imaging system 520, an indication of a first intensity at some or all of the plurality of sites while the temperature of the contents of the fluidic channel 515 is within the first temperature range. The processor 505 may instruct the heater 510 to set the temperature within the fluidic channel to be within the second temperature range. The processor 505 may then obtain, from the imaging system 520, an indication of a second intensity at some or all of the plurality of sites while the temperature of the fluidic channel 515 is within the second temperature range. In response to the first intensity at a particular site of the plurality of sites being less than a first value, and the second intensity at the particular site being greater than or equal to a second value, the processor 505 may determine that a first fluorescently-labeled nucleotide precursor has been incorporated into an extendable primer at the particular site. For example, if the processor 505 determines that the intensity at the particular site corresponds to the fluorescent label attached to an adenine precursor, the processor 505 may identify adenine as the detected label, or thymine as the next base in the fragment of nucleic acid being sequenced. Alternatively, in response to the first intensity at the particular site being greater than or equal to the first value, and the second intensity at the particular site being greater than or equal to the second value and less than a third value, the third value being greater than each of the first and second values, the processor 505 may determine that a second fluorescently-labeled nucleotide precursor has been incorporated into the extendable primer at the particular site. Finally, in response to the first intensity at the particular site being greater than or equal to the first value, and the second intensity at the particular site being greater than or equal to the third value, the processor 505 may determine that a third fluorescently-labeled nucleotide precursor has been incorporated into the extendable primer at the particular site.

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

As used in the specification and the appended claims, the singular forms "a," "an" and "the" do not exclude plural referents unless otherwise specified. The word "or" is to be interpreted as inclusive unless otherwise specified. Thus, the phrase "A or B" is to be interpreted as meaning all of the following: "both A and B," "A but not B," and "B but not A." Any use of "and/or" herein does not mean that the word "or" alone connotes exclusivity.

As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

To the extent that the terms "include(s)," "having," "has," "with," and variants thereof are used in the detailed description or the claims, such terms are intended to be inclusive in a manner similar to the term "comprising," i.e., meaning "including but not limited to." The terms "exemplary" and "embodiment" are used to express examples, not preferences or requirements.

The drawings are not necessarily to scale, and the dimensions, shapes, and sizes of the features may differ substantially from how they are depicted in the drawings.

Although specific embodiments have been disclosed, it will be evident that various modifications and changes may be made thereto without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

We claim:

1. A system for sequencing nucleic acid, comprising:
a fluidic channel having a plurality of sites for attaching, to a surface of the fluidic channel, a plurality of nucleic acid strands to be sequenced;
a heater coupled to the fluidic channel for setting a temperature of a contents of the fluidic channel to be within any of first, second, third, and fourth temperature ranges, wherein the first, second, third, and fourth temperature ranges are non-overlapping;
an imaging system configured to detect an intensity of light emitted at each of the plurality of sites; and
at least one processor coupled to the imaging system and to the heater and configured to execute at least one machine-readable instruction that, when executed, causes the at least one processor to:
in response to an intensity of light emitted at a particular site of the plurality of sites satisfying a first rule, identify a first fluorescently-labeled nucleotide precursor or a complementary base of the first fluorescently-labeled nucleotide precursor, and
in response to the intensity of light emitted at the particular site of the plurality of sites satisfying a second rule, identify a second fluorescently-labeled nucleotide precursor or a complementary base of the second fluorescently-labeled nucleotide precursor.

2. The system of claim 1, wherein the first rule is that the intensity of light emitted at the particular site is greater than or equal to a first threshold in the first temperature range and in the second temperature range, and the second rule is that the intensity of light emitted at the particular site is less than a second threshold in the first temperature range and greater than or equal to the second threshold in the second temperature range.

3. The system of claim 2, wherein:
the second temperature range is lower than the first temperature range.

4. The system of claim 1, wherein, when executed, the at least one machine-readable instruction further causes the at least one processor to:
in response to the intensity of light emitted at the particular site of the plurality of sites satisfying a third rule, identify a third fluorescently-labeled nucleotide precursor or a complementary base of the third fluorescently-labeled nucleotide precursor.

5. The system of claim 4, wherein:
the first rule is that the intensity of light emitted at the particular site is greater than or equal to a first threshold in the first temperature range and in the second temperature range,
the second rule is that the intensity of light emitted at the particular site is less than a second threshold in the first temperature range and greater than or equal to the second threshold in the second temperature range, and
the third rule is that the intensity of light emitted at the particular site is less than a third threshold in the first and second temperature ranges and greater than or equal to the third threshold in the third temperature range.

6. The system of claim 5, wherein:
the second temperature range is lower than the first temperature range, and
the third temperature range is lower than the second temperature range.

7. The system of claim 4, wherein, when executed, the at least one machine-readable instruction further causes the at least one processor to:
in response to the intensity of light emitted at the particular site of the plurality of sites satisfies a fourth rule, identify a fourth fluorescently-labeled nucleotide precursor or a complementary base of the fourth fluorescently-labeled nucleotide precursor.

8. The system of claim 7, wherein:
the first rule is that the intensity of light emitted at the particular site is greater than or equal to a first threshold in the first temperature range and in the second temperature range,
the second rule is that the intensity of light emitted at the particular site is less than a second threshold in the first temperature range and greater than or equal to the second threshold in the second temperature range,
the third rule is that the intensity of light emitted at the particular site is less than a third threshold in the first and second temperature ranges and greater than or equal to the third threshold in the third temperature range, and
the fourth rule is that the intensity of light emitted at the particular site is less than a fourth threshold in each of the first, second, and third temperature ranges and greater than or equal to a fourth threshold in the fourth temperature range.

9. The system of claim 8, wherein:
the second temperature range is lower than the first temperature range,
the third temperature range is lower than the second temperature range, and
the fourth temperature range is lower than the third temperature range.

10. The system of claim 1, wherein the fluidic channel comprises a structure, wherein the structure comprises the plurality of sites for attaching, to the surface of the fluidic channel, the plurality of nucleic acid strands to be sequenced.

11. The system of claim 10, wherein the structure comprises a cavity or a ridge.

12. The system of claim 1, wherein the heater comprises a thermal sensor or a microprocessor.

13. The system of claim 1, wherein the imaging system comprises one or more of: a camera, a light source, illumination optics, a detector, an optical blocking filter, an analog-to-digital converter (ADC), or one or more sensors.

14. The system of claim 13, wherein the imaging system comprises the light source, and wherein the light source comprises a laser.

15. The system of claim 13, wherein the imaging system comprises the illumination optics, and wherein the illumination optics are configured to distribute excitation light substantially uniformly over the plurality of sites.

16. The system of claim 13, wherein the imaging system comprises the detector, and wherein the detector comprises a lens.

17. The system of claim 16, wherein the imaging system comprises the optical blocking filter, and wherein the optical blocking filter is situated within the system to substantially isolate the lens from excitation light emitted by the light source.

18. The system of claim 13, wherein the imaging system comprises the one or more sensors, and wherein the one or more sensors comprise a charge-coupled device (CCD) sensor.

19. The system of claim 1, wherein, when executed by the at least one processor, the at least one machine-readable instruction further causes the at least one processor to control the heater and/or the imaging system.

20. The system of claim 1, wherein the heater comprises at least one heating element and at least one cooling element.

* * * * *